United States Patent
Vic et al.

(10) Patent No.: US 9,572,412 B2
(45) Date of Patent: Feb. 21, 2017

(54) HAIR SHAPING PROCESS USING FATTY SUBSTANCES, NON-SILICONE POLYMERS OR SURFACTANTS

(71) Applicant: L'OREAL, Paris (FR)

(72) Inventors: Gabin Vic, Semoy (FR); Maryse Chaisy, Goussainville (FR); Stefania Nuzzo, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/406,056

(22) PCT Filed: Jun. 6, 2013

(86) PCT No.: PCT/IB2013/054655
§ 371 (c)(1),
(2) Date: Dec. 5, 2014

(87) PCT Pub. No.: WO2013/183021
PCT Pub. Date: Dec. 12, 2013

(65) Prior Publication Data
US 2015/0128983 A1    May 14, 2015

Related U.S. Application Data

(60) Provisional application No. 61/701,648, filed on Sep. 15, 2012, provisional application No. 61/701,649, filed on Sep. 15, 2012, provisional application No. 61/701,650, filed on Sep. 15, 2012.

(30) Foreign Application Priority Data

Jun. 7, 2012 (FR) .................. 12 55307
Jun. 7, 2012 (FR) .................. 12 55309
Jun. 7, 2012 (FR) .................. 12 55310

(51) Int. Cl.
| | | |
|---|---|---|
| A61Q 5/04 | (2006.01) |
| A61Q 5/06 | (2006.01) |
| A45D 7/06 | (2006.01) |
| A61K 8/31 | (2006.01) |
| A61K 8/37 | (2006.01) |
| A61K 8/39 | (2006.01) |
| A61K 8/81 | (2006.01) |
| A61K 8/92 | (2006.01) |
| A61K 8/18 | (2006.01) |
| A61K 8/73 | (2006.01) |

(52) U.S. Cl.
CPC . *A45D 7/06* (2013.01); *A61K 8/18* (2013.01); *A61K 8/31* (2013.01); *A61K 8/37* (2013.01); *A61K 8/39* (2013.01); *A61K 8/737* (2013.01); *A61K 8/817* (2013.01); *A61K 8/8152* (2013.01); *A61K 8/8182* (2013.01); *A61K 8/92* (2013.01); *A61K 8/927* (2013.01); *A61Q 5/04* (2013.01); *A61Q 5/06* (2013.01); *A61K 2800/30* (2013.01); *A61K 2800/81* (2013.01)

(58) Field of Classification Search
None
See application file for complete search history.

(56) References Cited

U.S. PATENT DOCUMENTS

| | | |
|---|---|---|
| 3,958,340 A | 5/1976 | Meyers |
| 4,710,609 A | 12/1987 | Switlicki |
| 4,743,726 A | 5/1988 | Hughes et al. |
| 4,952,360 A | 8/1990 | Gibbon |
| 5,030,820 A | 7/1991 | Gibbon |
| 5,286,949 A | 2/1994 | Simons |
| 5,494,598 A | 2/1996 | Hughes |
| 5,676,871 A | 10/1997 | Graves |
| 5,773,802 A | 6/1998 | Graves |
| 5,819,763 A | 10/1998 | Hallowell, II |

(Continued)

FOREIGN PATENT DOCUMENTS

| | | |
|---|---|---|
| FR | 2 472 382 | 7/1981 |
| FR | 2 959 917 A1 | 11/2011 |

(Continued)

OTHER PUBLICATIONS

International Search Report issued Oct. 22, 2013, in PCT/IB2013/054655, filed Jun. 6, 2013.

(Continued)

*Primary Examiner* — Jyothsna Venkat
(74) *Attorney, Agent, or Firm* — Oblon, McClelland, Maier & Neustadt, L.L.P.

(57) ABSTRACT

The invention relates to a cosmetic process for treating keratin fibers, preferably the hair, comprising at least the steps consisting in:

a) applying to said keratin fibers a composition containing at least one substance chosen from fatty substances, non-silicone polymers and surfactants, b) applying a mechanical tension to said keratin fibers, and c) exposing said keratin fibers under mechanical tension to microwaves, at a pressure ranging from 50 000 to 250 000 Pa, in the presence of at least one solvent in vapor form on contact with the keratin fibers and without there being complete drying of the keratin fibers throughout the entire exposure to the microwaves, the solvent(s) in vapor form being entirely generated by evaporating at least one compound present, before emission of the microwaves, on contact with the keratin fibers, step a) taking place prior to step c).

10 Claims, 4 Drawing Sheets

(56) References Cited

U.S. PATENT DOCUMENTS

| | | | |
|---|---|---|---|
| 5,988,182 | A | 11/1999 | Engelbrecht |
| 6,079,422 | A | 6/2000 | Drago et al. |
| 6,352,080 | B1 | 3/2002 | Neville |
| 2004/0250830 | A1 | 12/2004 | Mackinder |
| 2006/0042649 | A1 | 3/2006 | Anzevino |
| 2007/0020215 | A1* | 1/2007 | Mathonneau ............ A61K 8/63 424/70.7 |
| 2007/0056960 | A1 | 3/2007 | Bell |
| 2013/0152959 | A1 | 6/2013 | Genain et al. |

FOREIGN PATENT DOCUMENTS

| | | |
|---|---|---|
| WO | 02/051281 A2 | 7/2002 |
| WO | 02/100210 A2 | 12/2002 |
| WO | WO 2011/141882 * | 11/2011 |

OTHER PUBLICATIONS

French Preliminary Search Report issued Mar. 19, 2013, in Patent Application No. FR 1255307, filed Jun. 7, 2012 (with English Translation of Category of Cited Documents).

French Preliminary Search Report issued Mar. 19, 2013, in Patent Application No. FR 1255309, filed Jun. 7, 2012 (with English Translation of Category of Cited Documents).

French Preliminary Search Report issued Mar. 19, 2013, in Patent Application No. FR 1255310, filed Jun. 7, 2012 (with English Translation of Category of Cited Documents).

* cited by examiner

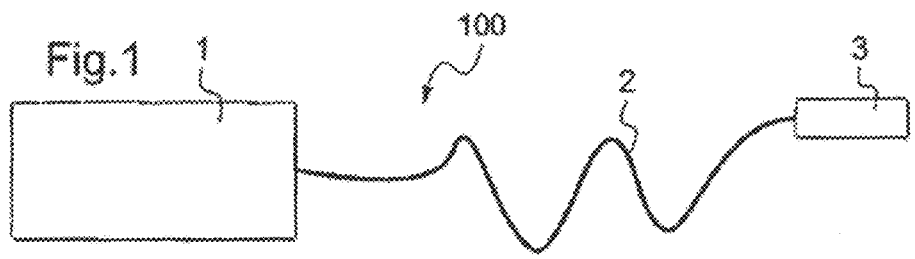
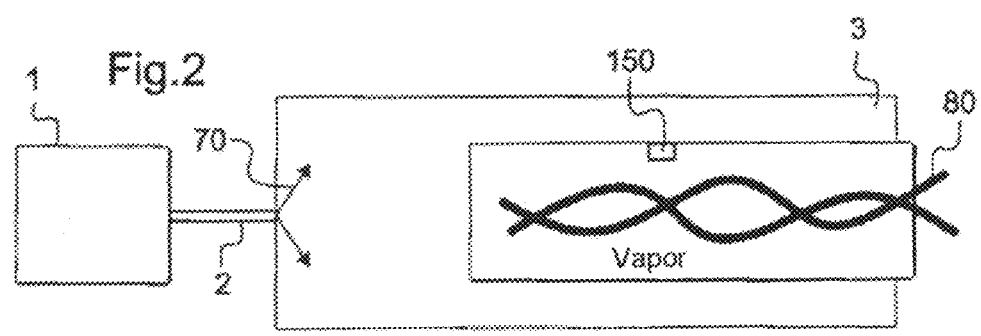
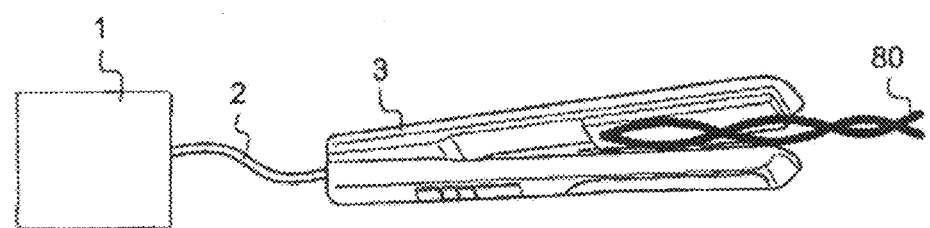
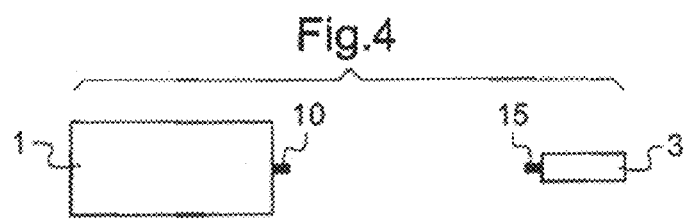
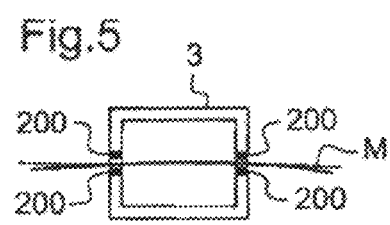
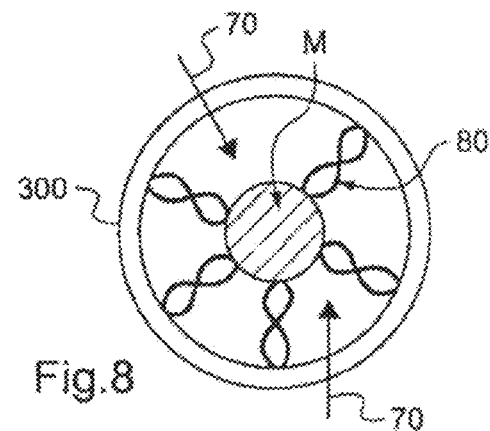

HAIR SHAPING PROCESS USING FATTY SUBSTANCES, NON-SILICONE POLYMERS OR SURFACTANTS

The present invention relates to the field of processes for treating keratin fibers, preferably the hair.

BACKGROUND

Cosmetic treatments for long-lasting shaping of the hair are mainly performed using chemical products.

Two techniques, both based on cleavage of the —S—S— disulfide bonds present in keratin (cystine) are generally used for obtaining permanent reshaping of the hair.

The first technique includes a first step that consists in opening the disulfide bonds using a composition comprising a reducing agent, for example of thioglycolic acid type. This first reduction step is generally performed at a pH of between 8 and 9.

This first technique then involves, preferably after rinsing the hair, a second step that consists in reconstituting the disulfide bonds by applying to the hair an oxidizing composition known as a fixer. The hair may, prior to the application of the reducing composition, be placed under tension by suitable devices such as curlers, or be straightened out. The oxidation step may in particular be performed at a pH of about 3 with hydrogen peroxide and may facilitate the formation of new disulfide bridges enabling the head of hair to be held in the desired shape.

The second technique involves a step of lanthionization using a composition comprising a base belonging to the family of hydroxides. The lanthionization step is generally performed at a basic pH of about 13. Lanthionization is the conversion of the disulfide bridges into monosulfide bridges. This type of treatment is mainly used for shaping naturally frizzy hair.

In order to obtain satisfactory performance in terms of durability of shaping, the compositions used in the treatments known in the prior art may comprise relatively high concentrations of chemical active agents (for example reducing agents or hydroxide compounds). Thus, thioglycolic acid may, for example, be used in certain compositions, at mass concentrations of between 6% and 11%, and sodium hydroxide at 2%.

Products comprising thioglycolic acid have an unpleasant odor, which may be present during the application and may also persist on the hair once the treatment has been performed.

In addition, the treatments described above may lead to irreversible degradation of the hair induced by changes in the intrinsic properties of the hair fiber.

These treatments may also irritate the scalp due to their relatively high concentration of chemical active agents.

It is moreover known practice to supply heat during the treatment in order to activate the processes. These techniques may effectively make it possible to improve the cosmetic performance qualities, but always involve high concentrations of chemical active agents and may thus have the same drawbacks as the treatments described above.

Documents WO 2002/051 281, US 2006/0 042 649, US 2004/0 250 830, WO 2002/100 210, US 2000/680 432, U.S. Pat. Nos. 6,079,422, 5,988,182, 5,819,763, 5,773,802, 5,676,871, JP 09075125, JP 09051813, AU 9664467, U.S. Pat. No. 5,494,598, EP 197 824, U.S. Pat. Nos. 4,710,609, 4,743,726, 4,952,360, 5,030,820 and 5,286,949 describe objects, for example curlers, which may be heated in a household microwave oven and used on wet hair for drying and hairsetting.

U.S. Pat. No. 3,958,340 describes a process for the rapid drying of wigs using air heated by microwave radiation.

Patent application US 2007/0 056 960 describes a shaping tool for curling, straightening and drying locks of wet hair using microwaves.

Patent DE 3148538 describes a cylindrical tool, protected with a wall, around which a lock of hair is wound. The lock is dried and set using microwaves applied in the space between the cylinder and the wall.

FR 2 178 049 discloses devices for releasing electromagnetic energy in various materials.

Moreover, processes for heating and drying the hair using electromagnetic radiation are known from FR 2 114 540 and FR 2 118 945.

Patent application FR 2 959 917 describes a hair treatment process in which a mechanical tension is applied to the hair, which is then exposed to microwaves.

There is a need for novel processes, which are more efficient and less aggressive, for permanently reshaping the hair.

There is especially interest in providing processes for obtaining improved lasting shaping performance, while at the same time minimizing the impact of chemical products on the hair and the scalp.

There is also a need to benefit from novel devices for lasting shaping of the hair.

The present invention is directed toward meeting all or some of the abovementioned needs.

According to a first aspect, the present invention relates to a cosmetic process for treating keratin fibers, preferably the hair, comprising at least the steps consisting in:

a) applying to said keratin fibers a composition containing at least one substance chosen from fatty substances, non-silicone polymers and surfactants, b) applying a mechanical tension to said keratin fibers, and c) exposing said keratin fibers under mechanical tension to microwaves, at a pressure ranging from 50 000 to 250 000 Pa, in the presence of at least one solvent in vapor form on contact with the keratin fibers and without there being complete drying of the keratin fibers throughout the entire exposure to the microwaves, the solvent(s) in vapor form being entirely generated by evaporating at least one compound present, before emission of the microwaves, on contact with the keratin fibers, step a) taking place prior to step c).

In the present text, the term "solvent" is used without preference to denote a single solvent or a mixture of solvents.

The process according to the present invention may be performed in order to lead to a durable shaping treatment that is less aggressive to the scalp and the hair. This is because the process according to the invention dispenses with the use of compounds that are aggressive to the scalp.

In addition, application to the hair of a composition containing at least one substance chosen from fatty substances, non-silicone polymers and surfactants, preferably prior to the application of a mechanical tension, in the presence of microwaves and of a solvent in vapor form, makes it possible to obtain durable and improved shaping of the hair without it being necessary to use reducing agents or alkali metal or alkaline-earth metal hydroxides.

In particular, the process according to the invention may use in step a) a composition containing at least one fatty substance or a composition containing at least one non-silicone polymer or a composition containing at least one surfactant.

Thus, according to one embodiment, the present invention is directed toward a cosmetic process for treating keratin fibers, preferably the hair, comprising at least the steps consisting in:

a) applying to said keratin fibers a composition containing at least one fatty substance, b) applying a mechanical tension to said keratin fibers, and c) exposing said keratin fibers under mechanical tension to microwaves, at a pressure ranging from 50 000 to 250 000 Pa, in the presence of at least one solvent in vapor form on contact with the keratin fibers and without there being complete drying of the keratin fibers throughout the entire exposure to the microwaves, the solvent(s) in vapor form being entirely generated by evaporating at least one compound present, before emission of the microwaves, on contact with the keratin fibers, step a) taking place prior to step c).

According to another embodiment, the present invention is directed toward a cosmetic process for treating keratin fibers, preferably the hair, comprising at least the steps consisting in:

a) applying to said keratin fibers a composition containing at least one non-silicone polymer, b) applying a mechanical tension to said keratin fibers, and c) exposing said keratin fibers under mechanical tension to microwaves, at a pressure ranging from 50 000 to 250 000 Pa, in the presence of at least one solvent in vapor form on contact with the keratin fibers and without there being complete drying of the keratin fibers throughout the entire exposure to the microwaves, the solvent(s) in vapor form being entirely generated by evaporating at least one compound present, before emission of the microwaves, on contact with the keratin fibers, step a) taking place prior to step c).

According to yet another embodiment, the present invention is directed toward a cosmetic process for treating keratin fibers, preferably the hair, comprising at least the steps consisting in:

a) applying to said keratin fibers a composition containing at least one surfactant, b) applying a mechanical tension to said keratin fibers, and c) exposing said keratin fibers under mechanical tension to microwaves, at a pressure ranging from 50 000 to 250 000 Pa, in the presence of at least one solvent in vapor form on contact with the keratin fibers and without there being complete drying of the keratin fibers throughout the entire exposure to the microwaves, the solvent(s) in vapor form being entirely generated by evaporating at least one compound present, before emission of the microwaves, on contact with the keratin fibers, step a) taking place prior to step c).

In one particular variant of the invention, the process according to the invention does not comprise a step of applying to the keratin fibers any composition(s) comprising alkali metal or alkaline-earth metal hydroxides at a pH above 12 or reducing agents for cleaving the disulfide bonds.

The process according to the invention allows a production of the desired shaping: curling or straightening. The effect is obtained durably for several weeks. When the process according to the invention is performed for obtaining curling, the curling obtained is uniform. A gain in the volume of the head of hair is also observed.

The terms "including a", "comprising a" and "containing a" should be understood as meaning "including at least one", "comprising at least one" and "containing at least one".

The term "at least one" is equivalent to the term "one or more".

The term "between" should be understood as being limits inclusive.

Step a)

The cosmetic hair treatment process according to the invention especially includes a step a) comprising the application of a composition containing at least one substance chosen from fatty substances, non-silicone polymers and surfactants.

Advantageously, the composition used in step a) is an aqueous composition, i.e. a composition comprising at least 5% by weight of water relative to the total weight of the composition. Preferably, the composition comprises from 20% to 99.9% by weight of water relative to the total weight of the composition.

According to a particular, preferred embodiment of the invention, step a) is prior to step b).

According to another particular embodiment of the invention, step b) is prior to step a).

According to a particularly preferred embodiment, the steps are performed in the following order: step a), then step b) and then step c).

In one particular variant of the invention, the process according to the invention does not comprise a step of applying to the keratin fibers any composition(s) comprising alkali metal or alkaline-earth metal hydroxides at a pH above 12 or reducing agents for cleaving the disulfide bonds. In this variant, the composition of step a) is free of reducing agent(s) for cleaving the disulfide bonds.

For the purposes of the invention, the expression "reducing agent for cleaving the disulfide bonds" means an agent chosen from thiols, alkali metal sulfites, phosphines and hydrides.

Similarly, in this variant, the composition of step a) is free of alkali metal or alkaline-earth metal hydroxides at a pH above 12.

The term "free of" means a composition comprising less than 0.5% by weight of the element under consideration, preferably less than 0.1% by weight relative to the total weight of the composition, and better still not containing any of the element under consideration.

Fatty Substances

According to a first embodiment variant of the invention, the composition of step a) is a composition containing at least one fatty substance. According to this first variant, the composition preferably comprises from 30% to 95% by weight of water relative to the total weight of the composition.

Preferably, said composition comprises at least one fatty substance in a content ranging from 0.1% to 95% by weight relative to the total weight of the composition.

According to a particular embodiment, said fatty substance(s) are present in said composition in a content ranging from 1% to 50% by weight and preferably from 5% to 30% by weight relative to the total weight of the composition.

The term "fatty substance" means an organic compound that is insoluble in water at ordinary temperature (25° C.) and at atmospheric pressure (760 mmHg), i.e. which has a solubility of less than 5%, preferably less than 1% and even more preferentially less than 0.1%. They have in their structure at least one sequence of at least two siloxane groups or a hydrocarbon-based chain containing at least 6 carbon atoms. In addition, the fatty substances are generally soluble in organic solvents under the same temperature and pressure conditions, for instance chloroform, ethanol, benzene, liquid petroleum jelly or decamethylcyclopentasiloxane.

In particular, the fatty substance(s) used in step a) are neither (poly)oxyalkylenated nor (poly)glycerolated.

More particularly, the fatty substance(s) are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, non-salified fatty acids, fatty acid and/or fatty alcohol esters other than triglycerides and plant waxes, non-silicone waxes and silicones, and mixtures thereof.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

Preferably, the fatty substance(s) used in step a) of the process according to the present invention are non-silicone fatty substances.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the cosmetic composition of step a) are saturated or unsaturated, linear or branched alcohols comprising from 6 to 30 carbon atoms and more particularly from 8 to 30 carbon atoms, among which mention may be made, for example, of cetyl alcohol, stearyl alcohol and the mixture thereof (cetylstearyl alcohol or cetearyl alcohol), octyldodecanol, 2-butyloctanol, 2-hexyldecanol, 2-undecylpentadecanol, oleyl alcohol or linoleyl alcohol.

The non-salified fatty acids that may be used in the cosmetic composition of step a) may be saturated or unsaturated carboxylic acids comprising from 6 to 30 carbon atoms and in particular from 9 to 30 carbon atoms. They are more particularly chosen from myristic acid, palmitic acid, stearic acid, behenic acid, oleic acid, linoleic acid, linolenic acid and isostearic acid.

These acids are not salified. This means that they are introduced in the form of free acids and that the composition does not comprise any alkaline agent leading to their salification.

The esters of fatty acids and/or of fatty alcohols, advantageously different from the triglycerides mentioned above, which may be used in the cosmetic composition used in step a) are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition used in step a) of the process according to the invention may also comprise, as fatty ester, sugar esters and diesters of $C_6$-$C_{30}$ and preferably $C_{12}$-$C_{22}$ fatty acids. It is recalled that the term "sugar" means oxygenous hydrocarbon-based compounds that contain several alcohol functions, with or without aldehyde or ketone functions, and that comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and in particular mono- or di-oleate, -stearate, -behenate, -oleopalmitate, -linoleate, -linolenate or -oleostearate of sucrose, glucose or methylglucose.

An example that may be mentioned is the product sold under the name Glucate® DO by the company Amerchol, which is a methylglucose dioleate.

Examples of esters or mixtures of esters of sugar of fatty acid that may also be mentioned include:
 the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
 the products sold under the name Ryoto Sugar Esters, for example referenced B370 and corresponding to sucrose behenate formed from 20% monoester and 80% di-triester-polyester;
 the sucrose mono-di-palmitostearate sold by the company Goldschmidt under the name Tegosoft® PSE.

Use may also be made of esters of fatty acids and of fatty alcohols. An example that will be mentioned is the product sold under the name Crodamol MS-PA (MH) by the company Croda.

The non-silicone wax(es) that may be used in the cosmetic composition used in step a) are chosen especially from carnauba wax, candelilla wax, esparto grass wax, hydrocarbon waxes including paraffin wax, ozokerite and microcrystalline wax, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The silicones that may be used in step a) in accordance with the invention may be in the form of oils, waxes, resins or gums.

Preferably, the silicone(s) are chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They may be volatile or nonvolatile.

When they are volatile, the silicones are more particularly chosen from those with a boiling point of between 60° C. and 260° C., and even more particularly from:
 (i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxanes/methylalkylsiloxane type, such as Volatile Silicone® FZ 3109 sold by the company Union Carbide, of formula:

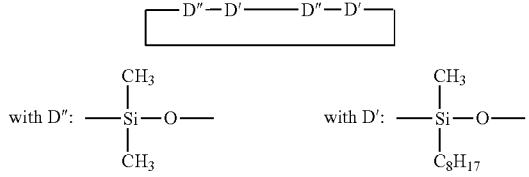

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;
 (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Use is preferably made of nonvolatile polydialkylsiloxanes, polydialkylsiloxane gums and resins, polyorganosiloxanes modified by the organofunctional groups above, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to Standard ASTM 445 Appendix C.

Among these polydialkylsiloxanes, mention may be made, in a nonlimiting manner, of the following commercial products:
 the Silbione® oils of the 47 and 70 047 series or the Mirasil® oils sold by Rhodia, for instance the oil 70 047 V 500 000;
 the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
the mixtures formed from a hydroxy-terminated polydimethylsiloxane or dimethiconol (CTFA) chain, and from a cyclic polydimethylsiloxane, also known as cyclomethicone (CTFA), such as the product Q2 1401 sold by the company Dow Corning;
mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs with different viscosities, and more particularly of a PDMS gum and of a PDMS oil, such as the product SF 1236 from the company General Electric. The product SF 1236 is a mixture of a gum SE 30 defined above with a viscosity of 20 m$^2$/s and of an oil SF 96 with a viscosity of $5\times10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

R2SiO2/2, R3SiO1/2, RSiO3/2 and SiO4/2 in which R represents an alkyl containing 1 to 16 carbon atoms. Particularly preferred among these products are those in which R denotes a C1-C4 lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure. Mention may also be made of the trimethylsiloxysilicate type resins sold in particular under the names X22-4914, X21-5034 and X21-5037 by the company Shin-Etsu.

The organomodified silicones that may be used in step a) are silicones as defined previously and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1\times10^{-5}$ to $5\times10^{-2}$ m$^2$/s at 25° C.

Among these polyalkylarylsiloxanes, examples that may be mentioned include the products sold under the following names:
the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Mention may also be made, among the organomodified silicones, of polyorganosiloxanes comprising:
substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are in particular C1-C4 aminoalkyl groups;
alkoxylated groups, such as the product sold under the name Silicone Copolymer F-755 by SWS Silicones, and Abil Wax® 2428, 2434 and 2440 by the company Goldschmidt.

Preferably, the fatty substance(s) used in the composition according to the invention are non-silicone fatty substances.

In one variant of the invention, the fatty substance(s) are chosen from compounds that are liquid or pasty at room temperature (25° C.) and at atmospheric pressure.

In this variant, preferably, the fatty substance(s) are compounds that are liquid at room temperature (25° C.) and at atmospheric pressure.

Even more preferentially, in this variant, the fatty substance(s) used in the composition used in step a) according to the invention are liquid and non-silicone at a temperature of 25° C. and at atmospheric pressure.

Still in this variant, the fatty substance(s) are advantageously chosen from $C_6$-$C_{16}$ hydrocarbons, hydrocarbons containing more than 16 carbon atoms, triglycerides, fatty alcohols, esters of a fatty acid and/or of a fatty alcohol other than triglycerides, or mixtures thereof.

Preferably, in this variant, the fatty substance(s) are chosen from liquid petroleum jelly, polydecenes, liquid fatty alcohols and liquid esters of fatty acids and/or of fatty alcohols, or mixtures thereof.

In another variant of the invention, the fatty substance(s) are chosen from compounds that are solid at room temperature (25° C.) and at atmospheric pressure.

In this variant, the fatty substance(s) are advantageously chosen from hydrocarbon waxes, plant waxes, solid fatty alcohols and solid esters of fatty acids and/or of fatty alcohols, or mixtures thereof.

Non-silicone Polymers

According to a second embodiment variant of the invention, the composition of step a) is a composition containing at least one non-silicone polymer.

According to this second variant, the composition preferably comprises from 25% to 95% by weight of water and in particular from 30% to 90% by weight of water relative to the total weight of the composition.

Preferably, said composition comprises at least one non-silicone polymer in a content ranging from 0.01% to 95% by weight relative to the total weight of the composition.

According to a particular embodiment, said non-silicone polymer(s) are present in said composition in a content ranging from 0.1% to 50% by weight and preferably from 1% to 30% by weight relative to the total weight of the composition.

For the purposes of the invention, the non-silicone polymer(s) used in step a) may be chosen from thickening, fixing or conditioning polymers.

The term "thickening polymer" means a polymer which, when introduced at 1% by weight into a composition not containing it, makes it possible to increase the viscosity thereof by at least 100 cps and preferably at least 500 cps, at 25° C. and at a shear rate of 1 s$^{-1}$. This viscosity may be measured using a cone/plate viscometer (Haake R600 rheometer or the like).

Preferably, use will be made of a polymer which, when introduced at 1% by weight in an aqueous solution or an aqueous-alcoholic solution containing 30% ethanol, and at pH 7, or in an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of 1 s$^{-1}$. This viscosity may be measured using a cone/plate viscometer (Haake R600 rheometer or the like).

The thickening polymers may thicken the aqueous phase and/or the fatty phase, preferentially the aqueous phase.

The thickening polymer(s) used in step a) may be chosen from cellulose-based thickeners, especially hydroxyethylcellulose, hydroxypropylcellulose or carboxymethylcellulose, guar gum and derivatives thereof, especially hydroxypropyl guar, gums of microbial origin, especially xanthan gum or scleroglucan gum, crosslinked acrylic acid or acrylamidopropanesulfonic acid homopolymers, and associative polymers.

A hydroxypropyl guar that will be mentioned, for example, is the product sold by the company Rhodia under the trade name Jaguar HP 105.

As regards the associative thickeners, one or more polymers of nonionic or ionic nature may be used. Preferably, the associative thickeners are nonionic, anionic or cationic.

The chemical structure of the associative polymers (or amphiphilic polymers) more particularly comprises at least one hydrophilic region and at least one hydrophobic region. The term "hydrophobic group" means a radical or polymer with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the anionic amphiphilic thickening polymers comprising at least one fatty chain (hydrophobic) used in step a), mention may be made of:

(I) polymers comprising at least one hydrophilic unit, and at least one fatty-chain allyl ether unit, more particularly those whose hydrophilic unit is formed by an unsaturated ethylenic anionic monomer, advantageously by a vinylcarboxylic acid and most particularly by an acrylic acid or a methacrylic acid or mixtures thereof, and whose fatty-chain allyl ether unit corresponds to the monomer of formula (A) below:

$$CH_2=CR'CH_2OB_nR \qquad (A)$$

in which R' denotes H or CH3, B denotes an ethylenoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms. The unit of formula (A) that is more particularly preferred is a unit in which R' denotes H, n is equal to 10, and R denotes a stearyl radical (C18).

Among these fatty-chain anionic polymers, those that are preferred are polymers formed from 20% to 60% by weight of acrylic acid and/or methacrylic acid, 5% to 60% by weight of lower alkyl (meth)acrylates, 2% to 50% by weight of fatty-chain allyl ether of formula (A), and 0 to 1% by weight of a crosslinking agent that is a well-known copolymerizable polyethylenically unsaturated monomer, for instance diallyl phthalate, allyl (meth)acrylate, divinylbenzene, (poly)ethylene glycol dimethacrylate or methylenebisacrylamide.

Among the latter polymers, the ones that are most particularly preferred are crosslinked terpolymers of methacrylic acid, of ethyl acrylate, of polyethylene glycol (10 EO) stearyl ether (Steareth 10), especially those sold by the company Allied Colloids under the names Salcare SC 80 and Salcare SC 90, which are aqueous emulsions containing 30% of a crosslinked terpolymer of methacrylic acid, of ethyl acrylate and of steareth-10 allyl ether (40/50/10).

(II) polymers comprising at least one hydrophilic unit of unsaturated olefinic carboxylic acid type, and at least one hydrophobic unit of the type such as a (C10-C30) alkyl ester of an unsaturated carboxylic acid.

These polymers are preferably chosen from those in which the hydrophilic unit of unsaturated olefinic carboxylic acid type corresponds to the monomer of formula (B) below:

in which R1 denotes H or CH3 or C2H5, i.e. acrylic acid, methacrylic acid or ethacrylic acid units, and whose hydrophobic unit of the type such as a (C10-C30) alkyl ester of an unsaturated carboxylic acid corresponds to the monomer of formula (C) below:

in which R2 denotes H or CH3 or C2H5 (i.e. acrylate, methacrylate or ethacrylate units) and preferably H (acrylate units) or CH3 (methacrylate units), R3 denoting a C10-C30 and preferably C12-C22 alkyl radical.

The (C10-C30)alkyl esters of unsaturated carboxylic acids are, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Among the fatty-chain anionic polymers of this type, the ones that will be used more particularly are polymers formed from a mixture of monomers comprising:
(i) essentially acrylic acid,
(ii) an ester of formula (C) described above and in which R2 denotes H or $CH_3$, R3 denoting an alkyl radical containing from 12 to 22 carbon atoms,
(iii) and a crosslinking agent, which is a well-known copolymerizable polyethylenic unsaturated monomer, for instance diallyl phthalate, allyl (meth)acrylate, divinylbenzene, (poly)ethylene glycol dimethacrylate or methylenebisacrylamide.

Among the fatty-chain anionic polymers of this type, use will be made more particularly of those formed from 95% to 60% by weight of acrylic acid (hydrophilic unit), 4% to 40% by weight of C10-C30 alkyl acrylate (hydrophobic unit) and 0 to 6% by weight of crosslinking polymerizable monomer, or alternatively those formed from 98% to 96% by weight of acrylic acid (hydrophilic unit), 1% to 4% by weight of C10-C30 alkyl acrylate (hydrophobic unit) and 0.1% to 0.6% by weight of crosslinking polymerizable monomer such as those described previously.

Among said polymers above, the ones most particularly preferred according to the present invention are the carbomer product sold by the company Lubrizol under the name Carbopol Ultrez 10, and also the products sold by the company Goodrich under the trade names Pemulen TR1, Pemulen TR2, Carbopol 1382, and even more preferentially Pemulen TR1, and the product sold by the company SEPPIC under the name Coatex SX.

(III) maleic anhydride/C30-C38 α-olefin/alkyl maleate terpolymers, such as the product (maleic anhydride/C30-C38 α-olefin/isopropyl maleate copolymer) sold under the name Performa V 1608 by the company Newphase Technologies.

(IV) acrylic terpolymers comprising:
(a) 20% to 70% by weight of an α,β-monoethylenically unsaturated carboxylic acid,
(b) 20% to 80% by weight of a non-surfactant α,β-monoethylenically unsaturated monomer other than (a),
(c) 0.5% to 60% by weight of a nonionic monourethane, which is the product of reaction of a monohydric surfactant with a monoethylenically unsaturated monoisocyanate,
such as those described in patent application EP-A-0 173 109 and more particularly a methacrylic acid/methyl acrylate/dimethyl-meta-isopropenylbenzyl isocyanate terpolymer of ethoxylated (40 EO) behenyl alcohol as an aqueous 25% dispersion.

(V) copolymers comprising among their monomers an α,β-monoethylenically unsaturated carboxylic acid and an ester of an α,β-monoethylenically unsaturated carboxylic acid and of an oxyalkylenated (C8-C30) fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22 sold by the company Röhm & Haas, which is a methacrylic acid/ethyl acrylate/oxyalkylenated stearyl methacrylate terpolymer.

The fatty-chain (hydrophobic) nonionic amphiphilic thickening polymer(s) used in step a) are preferably chosen from:

(1) celluloses modified with groups comprising at least one fatty chain, especially such as:
hydroxyethylcelluloses modified with groups comprising at least one fatty chain, such as alkyl, arylalkyl or alkylaryl groups, or mixtures thereof, and in which the alkyl groups are preferably C8-C22, for instance the product Natrosol Plus Grade 330 CS (C16 alkyl) sold by the company Aqualon, or the product Bermocoll EHM 100 sold by the company Berol Nobel,
hydroxyethylcelluloses modified with alkylphenyl polyalkylene glycol ether groups, such as the product Amercell Polymer HM1500 (nonylphenyl polyethylene glycol (15) ether) sold by the company Amerchol, (2) hydroxypropyl guars modified with groups comprising at least one fatty chain, such as the product Esaflor HM 22 (C22 alkyl chain) sold by the company Lamberti, and the products RE210-18 (C14 alkyl chain) and RE205-1 (C20 alkyl chain) sold by the company Rhône-Poulenc, (3) chemically modified or unmodified starches, in particular distarch phosphates and carboxymethylstarch, (4) copolymers of vinylpyrrolidone and of fatty-chain hydrophobic monomers, with, for example:
the products Antaron V216 or Ganex V216 (vinylpyrrolidone/hexadecene copolymer) sold by the company ISP,
the products Antaron V220 or Ganex V220 (vinylpyrrolidone/eicosene copolymer) sold by the company ISP, (5) copolymers of C1-C6 alkyl methacrylates or acrylates and of amphiphilic monomers comprising at least one fatty chain, for instance the oxyethylenated methyl acrylate/stearyl acrylate copolymer sold by the company Goldschmidt under the name Antil 208, (6) copolymers of hydrophilic methacrylates or acrylates and of hydrophobic monomers comprising at least one fatty chain, for instance the polyethylene glycol methacrylate/lauryl methacrylate copolymer, (7) polymers comprising an aminoplast ether backbone having at least one fatty chain, such as the Pure Thix compounds sold by Süd-Chemie, (8) polyurethane polyethers comprising in their chain both hydrophilic blocks usually of polyoxyethylenated nature and hydrophobic blocks, which may be aliphatic sequences alone and/or cycloaliphatic and/or aromatic sequences.

Preferably, the polyurethane polyethers comprise at least two hydrocarbon-based fatty chains containing from 8 to 30 carbon atoms, separated by a hydrophilic block, the hydrocarbon-based chains possibly being pendent chains or chains at the end of the hydrophilic block.

As examples of fatty-chain nonionic polyurethane polyethers that may be used in step a) of the invention, use may be made of Rheolate 205 containing a urea function, sold by the company Rheox, or Rheolate 208, 204 or 212, and also Acrysol RM 184, Aculyn or Acrysol 44 and Aculyn or Acrysol 46 from the company Röhm & Haas [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Mention may also be made of the product Elfacos T210 containing a C12-C14 alkyl chain and the product Elfacos T212 containing a C18 alkyl chain, from Akzo, and also the product DW 1206B from Röhm & Haas, containing a C20 alkyl chain and a urethane bond, sold at a solids content of 20% in water.

Use may also be made of solutions or dispersions of these polymers, especially in water or in aqueous-alcoholic medium. Examples of such polymers that may be mentioned are Rheolate 255, Rheolate 278 and Rheolate 244 sold by the company Rheox. Use may also be made of the products DW 1206F and DW 1206J sold by the company Röhm & Haas.

The polyurethane polyethers that may be used according to the invention are in particular those described in the article by G. Formum, J. Bakke and Fk. Hansen—Colloid Polym. Sci., 271, 380-389 (1993).

The cationic amphiphilic polymers comprising at least one fatty chain (hydrophobic) used in step a) may especially be chosen from quaternized cellulose derivatives, cationic polyurethanes and cationic polyvinyllactams, and preferably from quaternized cellulose derivatives.

As examples of polymers of this type, mention may be made in particular of:
  quaternized celluloses modified with groups comprising at least one fatty chain, such as alkyl, arylalkyl or alkylaryl groups comprising at least 8 carbon atoms, or mixtures thereof,
  quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing C8-C30 fatty chains that may be indicated include the products Quatrisoft LM 200, Quatrisoft LM-X529-18-A, Quatrisoft LM-X529-18B (C12 alkyl) and Quatrisoft LM-X529-8 (C18 alkyl) sold by the company Amerchol and the products Crodacel QM, Crodacel QL (C12 alkyl) and Crodacel QS (C18 alkyl) sold by the company Croda.

All the anionic, cationic, amphoteric and nonionic fixing polymers and mixtures thereof used in the art may be used in the composition of step a) according to the present application.

The term "fixing polymer" means any polymer that is capable of giving a shape to a head of hair or of holding a head of hair in a given shape.

The fixing polymers may be soluble in the cosmetically acceptable medium or insoluble in this same medium and used in this case in the form of dispersions of solid or liquid particles of polymer (latex or pseudolatex).

The anionic fixing polymer(s) generally used are polymers comprising groups derived from carboxylic acid, sulfonic acid or phosphoric acid and have a number-average molecular mass of between approximately 500 and 5 000 000.

The carboxylic groups are provided by unsaturated mono- or dicarboxylic acid monomers, such as those corresponding to formula (I):

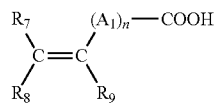

(I)

in which n is an integer from 0 to 10, $A_1$ denotes a methylene group optionally joined to the carbon atom of the unsaturated group or to the adjacent methylene group when n is greater than 1, via a heteroatom such as oxygen or sulfur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group, or a —$CH_2$—COOH, phenyl or benzyl group.

In the abovementioned formula, a lower alkyl group preferably denotes a group having 1 to 4 carbon atoms and in particular methyl and ethyl groups.

The anionic fixing polymers comprising carboxylic groups which are preferred according to the invention are:
  A) copolymers of acrylic or methacrylic acid or salts thereof, and of acrylamide, sold in the form of their sodium salts under the names Reten 421, 423 or 425 by the company Hercules;
  B) copolymers of acrylic or methacrylic acid with a monoethylenic monomer such as ethylene, styrene, vinyl esters and acrylic or methacrylic acid esters, optionally grafted onto a polyalkylene glycol such as polyethylene glycol and optionally crosslinked. Such polymers are described in particular in French patent 1 222 944 and German patent application 2 330 956, the copolymers of this type comprising an optionally N-alkylated and/or hydroxyalkylated acrylamide unit in their chain as described in particular in Luxembourg patent applications 75370 and 75371 or sold under the name Quadramer by the company American Cyanamid. Mention may also be made of copolymers of acrylic acid and of C1-C4 alkyl methacrylate and terpolymers of vinylpyrrolidone, of acrylic acid and of methacrylate of C1-C20 alkyl, for example lauryl methacrylate, such as the product sold by the company ISP under the name Acrylidone® LM and methacrylic acid/ethyl acrylate/tert-butyl acrylate terpolymers such as the product sold under the name Luvimer® 100 P by the company BASF;

Mention may also be made of methacrylic acid/acrylic acid/ethyl acrylate/methyl methacrylate copolymers as an aqueous dispersion, sold under the name Amerhold® DR 25 by the company Amerchol;
  C) crotonic acid copolymers, such as those comprising vinyl acetate or propionate units in their chain and optionally other monomers such as allyl esters or methallyl esters, vinyl ether or vinyl ester of a linear or branched saturated carboxylic acid with a long hydrocarbon-based chain, such as those containing at least 5 carbon atoms, it being possible for these polymers optionally to be grafted or crosslinked, or alternatively another vinyl, allyl or methallyl ester monomer of an α- or β-cyclic carboxylic acid. Such polymers are described, inter alia, in French patent Nos. 1 222 944, 1 580 545, 2 265 782, 2 265 781, 1 564 110 and 2 439 798. Commercial products coming within this category are the resins 28-29-30, 26-13-14 and 28-13-10 sold by National Starch;
  D) Copolymers of $C_4$-$C_8$ monounsaturated carboxylic acids or anhydrides chosen from:
    copolymers comprising (i) one or more maleic, fumaric or itaconic acids or anhydrides and (ii) at least one monomer selected from vinyl esters, vinyl ethers, vinyl halides, phenylvinyl derivatives, acrylic acid and its esters, the anhydride functions of these copolymers optionally being monoesterified or monoamidated. Such polymers are described, in particular, in U.S. Pat. Nos. 2,047,398, 2,723,248 and 2,102,113, and GB patent No. 839 805. Commercial products are in particular those sold under the names Gantrez® AN or ES by ISP;

copolymers comprising (i) one or more maleic, citraconic or itaconic anhydride units and (ii) one or more monomers chosen from allyl or methallyl esters, optionally comprising one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

These polymers are described, for example, in the Applicant's French patents 2 350 384 and 2 357 241.

E) Polyacrylamides comprising carboxylate groups.

The homopolymers and copolymers comprising sulfonic groups are polymers comprising vinylsulfonic, styrenesulfonic, naphthalenesulfonic or acrylamidoalkylsulfonic units.

These polymers may especially be selected from:
polyvinylsulfonic acid salts with a molecular mass of between 1000 and 100 000 approximately, and also the copolymers with an unsaturated comonomer such as acrylic or methacrylic acids and esters thereof, and also acrylamide or derivatives thereof, vinyl ethers and vinylpyrrolidone;
salts of polystyrenesulfonic acid, such as the sodium salts sold, for example, under the names Flexan® 500 and Flexan® 130 by National Starch. These compounds are described in patent FR 2 198 719;
polyacrylamidesulfonic acid salts, such as those mentioned in U.S. Pat. No. 4,128,631 and more particularly the polyacrylamidoethylpropanesulfonic acid sold under the name Cosmedia Polymer HSP 1180 by Henkel.

Mention may be made, as other anionic fixing polymer which can be used according to the invention, of the branched block anionic polymer sold under the name Fixate G-100 by Noveon.

According to the invention, the anionic fixing polymer(s) used in step a) are preferably chosen from acrylic acid copolymers such as the acrylic acid/ethyl acrylate/N-tert-butylacrylamide terpolymers sold in particular under the name Ultrahold® Strong by the company BASF, copolymers derived from crotonic acid, such as vinyl acetate/vinyl tert-butylbenzoate/crotonic acid terpolymers and the crotonic acid/vinyl acetate/vinyl neododecanoate terpolymers sold especially under the name Resin 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, under the name Gantrez® by the company ISP, the copolymers of methacrylic acid and of methyl methacrylate sold under the name Eudragit® L by the company Rohm Pharma, the copolymers of methacrylic acid and of ethyl acrylate sold under the name Luvimer® MAEX or MAE by the company BASF, the vinyl acetate/crotonic acid copolymers sold under the name Luviset CA 66 by the company BASF, the vinyl acetate/crotonic acid copolymers grafted with polyethylene glycol sold under the name Aristoflex® A by the company BASF, and the polymer sold under the name Fixate G-100 by the company Noveon.

Among the anionic fixing polymers mentioned above, it is more particularly preferred in the context of the present invention to use the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer® MAEX or MAE by the company BASF, the vinylpyrrolidone/acrylic acid/lauryl methacrylate terpolymers sold under the name Acrylidone® LM by the company ISP and the polymer sold under the name Fixate G-100 by the company Noveon.

The cationic fixing film-forming polymer(s) that may be used in step a) are preferably chosen from polymers comprising primary, secondary, tertiary and/or quaternary amine groups forming part of the polymer chain or directly connected to the latter, and having a molecular weight of between 500 and approximately 5 000 000 and preferably between 1000 and 3 000 000.

Among these polymers, mention may be made more particularly of the following cationic polymers:
(1) homopolymers or copolymers derived from acrylic or methacrylic esters or amides and comprising at least one of the units of the following formulae:

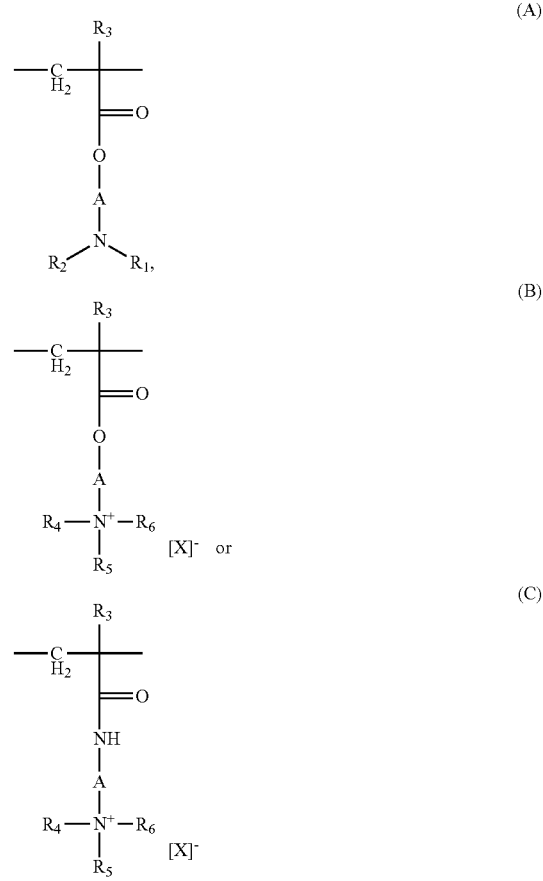

in which:
$R_3$ denotes a hydrogen atom or a $CH_3$ radical;
A is a linear or branched alkyl group comprising from 1 to 6 carbon atoms or a hydroxyalkyl group comprising from 1 to 4 carbon atoms;
$R_4$, $R_5$ and $R_6$, which may be identical or different, represent an alkyl group having from 1 to 18 carbon atoms or a benzyl radical;

$R_1$ and $R_2$, which may be identical or different, each represent a hydrogen atom or an alkyl group having from 1 to 6 carbon atoms;

X denotes a methosulfate anion or a halide, such as chloride or bromide.

The copolymers of family (1) also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyl-lactams such as vinylpyrrolidone or vinylcaprolactam, and vinyl esters.

Thus, among these copolymers of family (1), mention may be made of:
  copolymers of acrylamide and of dimethylaminoethyl methacrylate quaternized with dimethyl sulfate or with a dimethyl halide, such as the product sold under the name Hercofloc® by the company Hercules,
  copolymers of acrylamide and methacryloyloxyethyltrimethylammonium chloride, described for example in patent application EP-A-080976 and sold under the name Bina Quat P 100 by the company Ciba Geigy,
  copolymer of acrylamide and of methacryloyloxyethyltrimethylammonium methosulfate, such as that sold under the name Reten by Hercules,
  quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573,
  dimethylaminoethyl methacrylate/vinylcaprolactam/vinylpyrrolidone terpolymers, such as the product sold under the name Gaffix VC 713 by the company ISP, and
  quaternized vinylpyrrolidone/dimethylaminopropylmethacrylamide copolymers, such as the products sold under the name Gafquat® HS 100 by the company ISP.

(2) quaternary copolymers of vinylpyrrolidone and of vinylimidazole;

(3) chitosans or salts thereof; the salts which can be used are more particularly the acetate, lactate, glutamate, gluconate or pyrrolidone carboxylate of chitosan.

These compounds include the chitosan having a degree of deacetylation of 90.5% by weight which is sold under the name Kytan Brut Standard by the company Aber Technologies, and the chitosan pyrrolidone carboxylate which is sold under the name Kytamer® PC by the company Amerchol.

The commercial products corresponding to this definition are more particularly the products sold under the name Celquat L 200 and Celquat H 100 by the company National Starch.

The amphoteric fixing polymer(s) that may be used in step a) in accordance with the invention may be chosen from polymers comprising units B and C distributed statistically in the polymer chain, where B denotes a unit derived from a monomer comprising at least one basic nitrogen atom and C denotes a unit derived from an acid monomer comprising one or more carboxylic or sulfonic groups, or alternatively B and C may denote groups derived from carboxybetaine or sulfobetaine zwitterionic monomers;

B and C can also denote a cationic polymer chain comprising primary, secondary, tertiary or quaternary amine groups, in which at least one of the amine groups carries a carboxylic or sulfonic group connected via a hydrocarbon group, or alternatively B and C form part of a chain of a polymer comprising an α,β-dicarboxylic ethylene unit in which one of the carboxylic groups has been made to react with a polyamine comprising one or more primary or secondary amine groups.

The more particularly preferred amphoteric fixing polymers corresponding to the definition given above are chosen from the following polymers:

(1) copolymers containing acidic vinyl units and basic vinyl units, such as those resulting from the copolymerization of a monomer derived from a vinyl compound bearing a carboxylic group such as, more particularly, acrylic acid, methacrylic acid, maleic acid, α-chloroacrylic acid, and of a basic monomer derived from a substituted vinyl compound containing at least one basic atom, such as, more particularly, dialkylaminoalkyl methacrylate and acrylate, dialkylaminoalkylmethacrylamide and acrylamide. Such compounds are described in U.S. Pat. No. 3,836,537.

(2) Polymers comprising units derived from:
  a) at least one monomer chosen from acrylamides and methacrylamides substituted on the nitrogen atom with an alkyl group,
  b) at least one acidic comonomer containing one or more reactive carboxylic groups, and
  c) at least one basic comonomer such as esters with primary, secondary, tertiary and quaternary amine substituents of acrylic and methacrylic acids and the product of quaternization of dimethylaminoethyl methacrylate with dimethyl or diethyl sulfate.

The more particularly preferred N-substituted acrylamides or methacrylamides according to the invention are the compounds in which the alkyl groups comprise from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic, methacrylic, crotonic, itaconic, maleic or fumaric acid and also the monoesters of alkyl having from 1 to 4 carbon atoms of maleic or fumaric acid or anhydride.

The preferred basic comonomers are aminoethyl, butylaminoethyl, N,N'-dimethylaminoethyl and N-tert-butylaminoethyl methacrylates.

The copolymer whose CTFA (4th edition, 1991) name is octylacrylamide/acrylates/butylaminoethyl methacrylate copolymer, such as the products sold under the name Amphomer® or Lovocryl® 47 by the company National Starch, is particularly used.

(3) Partially or totally acylated and crosslinked polyaminoamides derived from polyaminoamides of general formula:

$$\text{—}\!\!\left[\text{CO—}R_{10}\text{—CO—Z}\right]\!\!\text{—} \tag{II}$$

in which R10 represents a divalent group derived from a saturated dicarboxylic acid, a mono- or dicarboxylic aliphatic acid containing an ethylenic double bond, an ester of a lower alkanol having 1 to 6 carbon atoms of these acids, or a group derived from the addition of any one of said acids to a bis(primary) or bis(secondary) amine, and Z denotes a group derived from a bis(primary), mono- or bis(secondary) polyalkylene-polyamine and preferably represents:
  a) in proportions of from 60 to 100 mol %, the group:

$$\text{—}\underset{H}{N}\text{—}\!\!\left[(CH_2)_x\text{—}\underset{H}{N}\right]_{\!p}\!\!\text{—} \tag{III}$$

where x=2 and p=2 or 3, or alternatively x=3 and p=2
this group being derived from diethylenetriamine, from triethylenetetramine or from dipropylenetriamine;

b) in proportions of from 0 to 40 mol %, the group (III) above in which x=2 and p=1 and which is derived from ethylenediamine, or the group derived from piperazine:

c) in proportions of from 0 to 20 mol %, the —NH—$(CH_2)_6$—NH— group derived from hexamethylenediamine, these polyaminoamides being crosslinked by addition reaction of a bifunctional crosslinking agent chosen from epihalohydrins, diepoxides, dianhydrides or bisunsaturated derivatives, by means of from 0.025 to 0.35 mol of crosslinking agent per amine group of the polyaminoamide, and acylated by reaction with acrylic acid, chloroacetic acid or an alkane sultone or their salts.

The saturated carboxylic acids are preferably chosen from acids having 6 to 10 carbon atoms, such as adipic acid, 2,2,4-trimethyladipic acid and 2,4,4-trimethyladipic acid, terephthalic acid, and acids containing an ethylenic double bond such as, for example, acrylic acid, methacrylic acid and itaconic acid.

The alkane sultones used in the acylation are preferably propane or butane sultone and the salts of the acylating agents are preferably the sodium or potassium salts.

(4) polymers comprising zwitterionic units of formula:

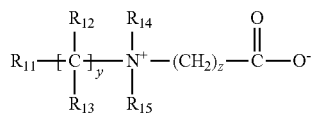

in which R11 denotes a polymerizable unsaturated group such as an acrylate, methacrylate, acrylamide or methacrylamide group, y and z represent an integer from 1 to 3, R12 and R13 represent a hydrogen atom, a methyl, ethyl or propyl group, R14 and R15 represent a hydrogen atom or an alkyl group such that the sum of the carbon atoms in R14 and R15 does not exceed 10.

The polymers comprising such units can also comprise units derived from non-zwitterionic monomers, such as dimethyl- or diethylaminoethyl acrylate or methacrylate or alkyl acrylates or methacrylates, acrylamides or methacrylamides, or vinyl acetate.

Mention may be made, by way of example, of methyl methacrylate/methyl dimethylcarboxymethylammonioethyl methacrylate copolymers, such as the product sold under the name Diaformer Z301 by Sandoz.

(5) polymers derived from chitosan comprising monomer units corresponding to the following formulae:

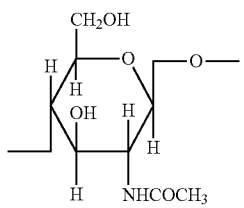

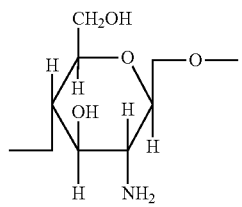

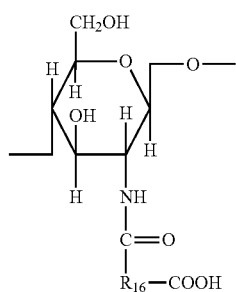

the unit (D) being present in proportions of between 0 and 30%, the unit (E) in proportions of between 5% and 50% and the unit (F) in proportions of between 30% and 90%, it being understood that, in this unit (F), R16 represents a group of formula:

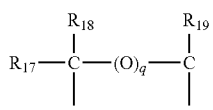

in which, if q=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, or an alkylthio residue in which the alkyl group bears an amino residue, at least one of the groups $R_{17}$, $R_{18}$ and $R_{19}$ being, in this case, a hydrogen atom;

or, if q=1, $R_{17}$, $R_{18}$ and $R_{19}$ each represent a hydrogen atom, and also the salts formed by these compounds with bases or acids;

(6) polymers comprising units corresponding to general formula (V) are described, for example, in French patent 1 400 366:

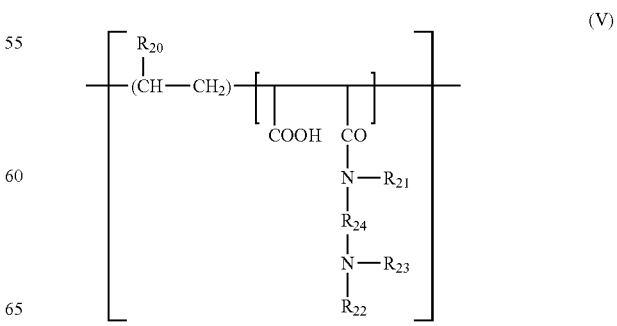

in which $R_{20}$ represents a hydrogen atom, a $CH_3O$, $CH_3CH_2O$ or phenyl group, $R_{21}$ denotes a hydrogen atom or a lower alkyl group such as methyl or ethyl, $R_{22}$ denotes a hydrogen atom or a $C_1$-$C_6$ lower alkyl group such as methyl or ethyl, $R_{23}$ denotes a $C_1$-$C_6$ lower alkyl group such as methyl or ethyl or a group corresponding to the formula: —$R_{24}$—$N(R_{22})_2$, $R_{24}$ representing a group —$CH_2$—$CH_2$—, —$CH_2$—$CH_2$—$CH_2$— or —$CH_2$—$CH(CH_3)$—, $R_{22}$ having the meanings mentioned above;

(7) Polymers derived from the N-carboxyalkylation of chitosan, such as N-(carboxymethyl)chitosan or N-(carboxybutyl)chitosan, which are sold under the "Evalsan" name by Jan Dekker.

(8) Amphoteric polymers of the -D-X-D-X— type chosen from:
a) polymers obtained by reaction of chloroacetic acid or sodium chloroacetate with compounds comprising at least one unit of formula:

-D-X-D-X-D-            (VI)

where D denotes a group

and X denotes the symbol E or E', E or E', which are identical or different, denoting a divalent group which is a straight- or branched-chain alkylene group comprising up to 7 carbon atoms in the main chain which is unsubstituted or substituted by hydroxyl groups and which can additionally comprise oxygen, nitrogen and sulfur atoms or from 1 to 3 aromatic and/or heterocyclic rings; the oxygen, nitrogen and sulfur atoms being present in the form of ether, thioether, sulfoxide, sulfone, sulfonium, alkylamine or alkenylamine groups or hydroxyl, benzylamine, amine oxide, quaternary ammonium, amide, imide, alcohol, ester and/or urethane groups,
b) polymers of formula:

-D-X-D-X—            (VI')

where D denotes a group

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate;

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers, such as vinylcaprolactam.

Among the amphoteric fixing polymers described above, the ones that are most particularly used in step a) according to the invention are those of family (3), such as the copolymers whose CTFA name is Octylacrylamide/acrylates/butylaminoethyl methacrylate copolymer, such as the products sold under the name Amphomer®, Amphomer® LV 71 or Lovocryl® 47 by the company National Starch and those of family (4) such as the copolymers of methyl methacrylate/methyl dimethylcarboxymethylammonioethyl methacrylate, sold, for example, under the name Diaformer Z301 by the company Sandoz.

The nonionic fixing polymer(s) that may be used in step a) according to the present invention are chosen, for example, from:
polyalkyloxazolines;
vinyl acetate homopolymers;
vinyl acetate copolymers, for instance copolymers of vinyl acetate and of acrylic ester, copolymers of vinyl acetate and of ethylene, or copolymers of vinyl acetate and of maleic ester, for example of dibutyl maleate;
acrylic ester homopolymers and copolymers, for instance copolymers of alkyl acrylates and of alkyl methacrylates, such as the products sold by the company Rohm & Haas under the names Primal® AC-261 K and Eudragit® NE 30 D, by BASF under the name 8845, or by the company Hoechst under the name Appretan® N9212;
copolymers of acrylonitrile and of a nonionic monomer chosen, for example, from butadiene and alkyl (meth)acrylates; mention may be made of the products sold under the name CJ 0601 B by the company Rohm & Haas;
styrene homopolymers;
styrene copolymers, for instance copolymers of styrene and of alkyl (meth)acrylate, such as the products Mowilith® LDM 6911, Mowilith® DM 611 and Mowilith® LDM 6070 sold by the company Hoechst, and the products Rhodopas® SD 215 and Rhodopas® DS 910 sold by the company Rhone-Poulenc; copolymers of styrene, of alkyl methacrylate and of alkyl acrylate; copolymers of styrene and of butadiene; or copolymers of styrene, of butadiene and of vinylpyridine;
polyamides;
vinyllactam homopolymers such as vinylpyrrolidone homopolymers and such as the polyvinylcaprolactam sold under the name Luviskol® Plus by the company BASF; and
vinyllactam copolymers such as a poly(vinylpyrrolidone/vinyllactam) copolymer sold under the trade name Luvitec® VPC 55K65W by the company BASF, poly (vinylpyrrolidone/vinyl acetate) copolymers, such as those sold under the name PVPVA® S630L by the company ISP, Luviskol® VA 73, VA 64, VA 55, VA 37 and VA 28 by the company BASF; and poly(vinylpyrrolidone/vinyl acetate/vinyl propionate) terpolymers, for instance the product sold under the name Luviskol® VAP 343 by the company BASF.

The alkyl groups of the nonionic polymers mentioned above preferably contain from 1 to 6 carbon atoms.

Use may also be made in step a), as fixing polymers, of functionalized or non-functionalized, cationic, nonionic, anionic or amphoteric polyurethanes, or mixtures thereof.

The polyurethanes that are particularly targeted by the present invention are those described in patent applications EP 0 751 162, EP 0 637 600, EP 0 648 485 and FR 2 743 297, of which the Applicant Company is the proprietor, and in patent applications EP 0 656 021 and WO 94/03510 from the company BASF and EP 0 619 111 from the company National Starch.

As polyurethanes that are particularly suitable in the present invention, mention may be made of the products sold under the name Luviset PUR® by the company BASF.

For the purposes of the present invention, the term "conditioning polymer" means a polymer that is capable of giving keratin fibers and in particular the hair an improvement of at least one of the following properties: softness of feel, straightening effect, ease of disentangling.

Preferably, the conditioning polymer(s) are cationic polymer(s) or amphoteric polymer(s), especially Polyquaternium-22.

Preferably, the conditioning polymer(s) are chosen from:

(1) cyclopolymers of alkyldiallylamine or of dialkyldiallylammonium salts, such as homopolymers or copolymers comprising, as main constituent of the chain, units corresponding to formula (VII) or (VIII):

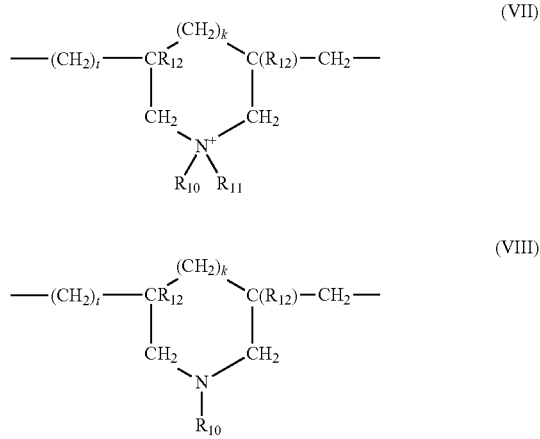

in which k and t are equal to 0 or 1, the sum k+t being equal to 1; R12 denotes a hydrogen atom or a methyl group; R10 and R11, independently of each other, denote an alkyl group having from 1 to 6 carbon atoms, a hydroxyalkyl group in which the alkyl group has preferably 1 to 5 carbon atoms, a lower (C1-C4) amidoalkyl group, or R10 and R11 may denote, jointly with the nitrogen atom to which they are attached, heterocyclic groups, such as piperidinyl or morpholinyl; Y— is an anion such as bromide, chloride, acetate, borate, citrate, tartrate, bisulfate, bisulfite, sulfate or phosphate. These polymers are especially described in French patent 2 080 759 and in its Certificate of Addition 2 190 406.

R10 and R11, independently of each other, preferably denote an alkyl group containing from 1 to 4 carbon atoms.

Among the polymers defined above, mention may be made more particularly of the dimethyldiallylammonium chloride homopolymer sold under the name Merquat 100 by the company Nalco and its homologues of low weight-average molecular weights, and the copolymers of diallyldimethylammonium chloride and of acrylamide sold under the name Merquat 550.

(2) quaternary diammonium polymers especially containing repeating units corresponding to formula (IX):

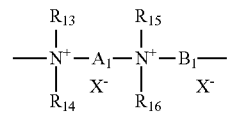

in which:

$R_{13}$, $R_{14}$, $R_{15}$ and $R_{16}$, which may be identical or different, represent aliphatic, alicyclic or arylaliphatic groups containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl group substituted with a nitrile, ester, acyl or amide group or a group CO—O—$R_{17}$-D or CO—NH—$R_{17}$-D where $R_{17}$ is an alkylene and D is a quaternary ammonium group, $A_1$ and $B_1$ represent polymethylene groups containing from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid, $A_1$, $R_{13}$ and $R_{15}$ can form, with the two nitrogen atoms to which they are attached, a piperazine ring. In addition, if A1 denotes a linear or branched, saturated or unsaturated alkylene or hydroxyalkylene radical, B1 may also denote a group (CH2)n-CO-D-OC—(CH2)p-, n and p are integers ranging from 2 to 20 approximately, in which D denotes:

a) a glycol residue of formula: —O—Z—O—, where Z denotes a linear or branched hydrocarbon-based radical or a group corresponding to one of the following formulae:

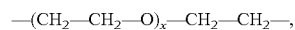

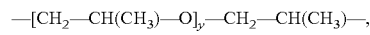

in which x and y denote an integer from 1 to 4, representing a defined and unique degree of polymerization or any number from 1 to 4 representing an average degree of polymerization, b) a bis-secondary diamine residue such as a piperazine derivative, c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—, d) a ureylene group of formula —NH—CO—NH—.

Preferably, $X^-$ is an anion such as chloride or bromide.

These polymers generally have a number-average molecular weight of between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (X):

$$-\underset{\underset{R_{19}}{|}}{\overset{\overset{R_{18}}{|}}{N^+}}-(CH_2)_r-\underset{\underset{R_{21}}{|}\ X^-}{\overset{\overset{R_{20}}{|}}{N^+}}-(CH_2)_s- \quad (X)$$

in which $R_{18}$, $R_{19}$, $R_{20}$ and $R_{21}$, which are identical or different, denote an alkyl or hydroxyalkyl group having from 1 to 4 carbon atoms approximately, r and s are integers ranging from 2 to 20 approximately, and $X^-$ is an anion derived from a mineral or organic acid.

A compound of formula (X) that is particularly preferred is the one for which R18, R19, R20 and R21 represent a methyl radical and r=3, s=6 and X=Cl, which is known as Hexadimethrine chloride according to INCI nomenclature (CTFA).

The quaternary diammonium polymers may also consist of units of formula (XI):

$$-\underset{\underset{R_{23}\ X^-}{|}}{\overset{\overset{R_{22}}{|}}{N^+}}-(CH_2)_t-NH-CO-(CH_2)_u-CO-NH-(CH_2)_v-\underset{\underset{R_{25}\ X^-}{|}}{\overset{\overset{R_{24}}{|}}{N^+}}-A- \quad (XI)$$

in which:

R22, R23, R24 and R25, which may be identical or different, represent a hydrogen atom or a methyl, ethyl, propyl, β-hydroxyethyl, β-hydroxypropyl or —CH2CH2 (OCH2CH2)pOH group, in which p is equal to 0 or to an integer between 1 and 6, with the proviso that R22, R23, R24 and R25 do not simultaneously represent a hydrogen atom, t and u, which may be identical or different, are integers between 1 and 6, v is equal to 0 or to an integer between 1 and 34, $X^-$ denotes an anion such as a halide, A denotes a radical of a dihalide or represents preferably —CH2-CH2-O—CH2-CH2-.

Such compounds are described especially in patent application EP-A-122 324.

Among these, mention may be made, for example, of the products Mirapol® A 15, Mirapol® AD1, Mirapol® AZ1 and Mirapol® 175, sold by the company Miranol.

(3) Cationic polysaccharides, especially cationic celluloses and galactomannan gums.

For celluloses, mention may be made of copolymers of cellulose or of cellulose derivatives grafted with a water-soluble monomer comprising a quaternary ammonium, and disclosed especially in U.S. Pat. No. 4,131,576, such as hydroxyalkylcelluloses, for example hydroxymethyl-, hydroxyethyl- or hydroxypropylcelluloses grafted in particular with a methacryloyloxyethyltrimethylammonium, methacrylamidopropyltrimethylammonium or dimethyldiallylammonium salt.

The products sold corresponding to this definition are, more particularly, the products sold under the names Celquat L 200, Celquat LOR and Celquat H 100 by the company Akzo Nobel (Polyquaternium-4). Mention may also be made of the product sold under the name Merquat 280 (Polyquaternium-22) by the company Lubrizol.

Surfactants

According to a third embodiment variant of the invention, the composition of step a) is a composition containing at least one surfactant.

According to this third variant, the composition preferably comprises from 30% to 70% by weight of water relative to the total weight of the composition.

Preferably, said composition comprises at least one surfactant in a content ranging from 0.01% to 95%, preferably from 0.1% to 60% and better still from 1% to 50% by weight relative to the total weight of the composition.

For the purposes of the invention, the surfactant(s) used in step a) may be chosen from nonionic surfactants, anionic surfactants, cationic surfactants and amphoteric or zwitterionic surfactants.

The surfactant(s) in accordance with the invention may be silicone or non-silicone surfactants.

The term "anionic surfactant" means a surfactant comprising, as ionic or ionizable groups, only anionic groups. These anionic groups are preferably chosen from the following groups: —C(O)OH, —C(O)O—, —SO$_3$H, —S(O)$_2$O—, —OS(O)$_2$OH, —OS(O)$_2$O—, —P(O)OH$_2$, —P(O)$_2$O—, —P(O)O$_2$—, —P(OH)$_2$, =P(O)OH, —P(OH)O—, =P(O)O—, =POH, =PO—; the anionic parts comprising a cationic counterion such as those of an alkali metal, an alkaline-earth metal or an ammonium.

As examples of anionic surfactants that may be used in step a) according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N-acyltaurates, salts of alkyl monoesters of polyglycoside-polycarboxylic acids, acyllactylates, D-galactoside-uronic acid salts, alkyl ether carboxylic acid salts, alkylaryl ether carboxylic acid salts, alkylamido ether carboxylic acid salts, and the corresponding non-salified forms of all these compounds, the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl ether monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Among the anionic surfactants mentioned, it is preferred to use ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

In particular, it is preferred to use $(C_{12}-C_{20})$alkyl sulfates, $(C_{12}-C_{20})$alkyl ether sulfates comprising from 2 to 20 ethylene oxide units, especially in the form of alkali metal, ammonium, amino alcohol and alkaline-earth metal salts, or a mixture of these compounds. Better still, it is preferred to use sodium lauryl ether sulfate containing 2.2 mol of ethylene oxide.

Examples of nonionic surfactants that may be used in step a) according to the invention are described, for example, in the *Handbook of Surfactants* by M. R. Porter, published by Blackie & Son (Glasgow and London), 1991, pp. 116-178). They are especially chosen from alcohols, α-diols and $(C_1-C_{20})$alkylphenols, these compounds being polyethoxylated, polypropoxylated and/or polyglycerolated, and containing at least one fatty chain comprising, for example, from 8 to 40 carbon atoms, it being possible for the number of ethylene oxide and/or propylene oxide groups to especially range from 1 to 200, and for the number of glycerol groups to especially range from 1 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, mono- or dialkanolamides, derivatives of N-alkyl glucamine and of N-acyl methylglucamine, aldobionamides, oxyethylenated and/or oxypropylenated silicones and amine oxides.

The nonionic surfactant(s) used in step a) are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
  oxyalkylenated $(C_8-C_{24})$alkylphenols,
  saturated or unsaturated, linear or branched, oxyalkylenated $C_8-C_{30}$ alcohols, especially such as Deceth-3 or Deceth-5,
  saturated or unsaturated, linear or branched, oxyalkylenated $C_8-C_{30}$ amides,
  esters of saturated or unsaturated, linear or branched, $C_8-C_{30}$ acids and of polyethylene glycols,
  polyoxyethylenated esters of saturated or unsaturated, linear or branched, $C_8-C_{30}$ acids and of sorbitol,
  saturated or unsaturated, oxyethylenated plant oils,
  condensates of ethylene oxide and/or of propylene oxide, inter alia, alone or as mixtures,
  oxyethylenated and/or oxypropylenated silicones.

The surfactant(s) bear a number of moles of ethylene oxide and/or of propylene oxide preferably ranging from 1 to 100 and better still from 2 to 50. Advantageously, the nonionic surfactant(s) do not comprise any oxypropylene units.

In accordance with a preferred embodiment of the invention, the nonionic surfactant(s) used in step a) are chosen from oxyethylenated $C_8-C_{30}$ alcohols and polyoxyethylenated esters of saturated or unsaturated, linear or branched, $C_8-C_{30}$ acids and of sorbitol.

As examples of monoglycerolated or polyglycerolated nonionic surfactants, monoglycerolated or polyglycerolated $C_8-C_{40}$ alcohols are preferably used in step a).

In particular, the monoglycerolated or polyglycerolated $C_8-C_{40}$ alcohols correspond to formula (A1) below:

$$RO\text{---}[\text{---}CH_2\text{---}CH(CH_2OH)\text{---}O]_m\text{---}H \quad (A1)$$

in which R represents a linear or branched $C_8-C_{40}$ and preferably $C_8-C_{30}$ alkyl or alkenyl radical, and m represents a number ranging from 1 to 30 and preferably from 1 to 10.

As examples of compounds that are suitable for use in step a) in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferably, the nonionic surfactant(s) are chosen from oxyethylenated or non-oxyethylenated alkanolamides and oxyethylenated fatty alcohols.

The cationic surfactant(s) that may be used in step a) comprise, for example, optionally polyoxyalkylenated primary, secondary or tertiary fatty amine salts, quaternary ammonium salts, and mixtures thereof.

Examples of quaternary ammonium salts that may especially be mentioned include:
  those corresponding to the general formula (A2) below:

in which formula (A2):
  $R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and
  $X^-$ represents an organic or mineral anionic counterion, such as that chosen from halides, acetates, phosphates, nitrates, $(C_1-C_4)$alkyl sulfates, $(C_1-C_4)$alkyl- or $(C_1-C_4)$alkylarylsulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1-C_{30}$ alkyl or alkenyl, $C_1-C_{30}$ alkoxy, polyoxy($C_2-C_6$)alkylene, $C_1-C_{30}$ alkylamide, $(C_{12}-C_{22})$alkylamido($C_2-C_6$)alkyl, $(C_{12}-C_{22})$alkyl acetate, and $C_1-C_{30}$ hydroxyalkyl groups; $X^-$ is an anionic counterion chosen from halides, phosphates, acetates, lactates, $(C_1-C_4)$alkyl sulfates, and $(C_1-C_4)$alkylsulfonates or $(C_1-C_4)$alkylarylsulfonates.

Among the quaternary ammonium salts of formula (A2), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A3) below:

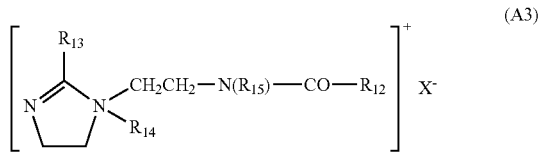

in which formula (A3):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or mineral anionic counterion, such as that chosen from halides, acetates, phosphates, lactates, ($C_1$-$C_4$)alkyl sulfates, ($C_1$-$C_4$)alkyl- or ($C_1$-$C_4$)alkylaryl sulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, in particular of formula (A4) below:

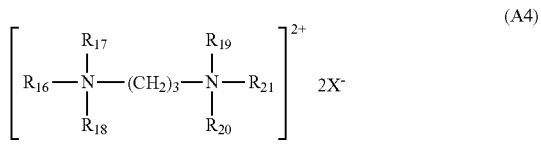

in which formula (A4):

$R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group $-(CH_2)_3-N^+(R_{16a})(R_{17a})(R_{18a})$, $X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)alkylaryl sulfonates, in particular methyl sulfate and ethyl sulfate.

Such compounds are, for example, Finquat CT-P, provided by the company Finetex (Quaternium 89), and Finquat CT, provided by the company Finetex (Quaternium 75);

quaternary ammonium salts containing one or more ester functions, such as those of formula (A5) below:

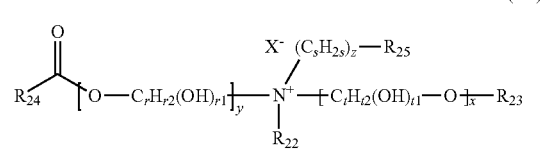

in which formula (A5):

$R_{22}$ is chosen from $C_1$-$C_6$ alkyl groups and $C_1$-$C_6$ hydroxyalkyl or dihydroxyalkyl groups, $R_{23}$ is chosen from:

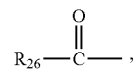

the group saturated or unsaturated and linear or branched $C_1$-$C_{22}$ hydrocarbon groups $R_{27}$, a hydrogen atom, $R_{25}$ is chosen from:

the group

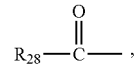

saturated or unsaturated and linear or branched $C_1$-$C_6$ hydrocarbon groups $R_{29}$, a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which are identical or different, are integers having values from 0 to 10, $X^-$ represents an organic or mineral anionic counterion, with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group and more particularly a methyl or ethyl group.

Advantageously, the sum x+y+z is from 1 to 10.

When $R_{23}$ is an $R_{27}$ hydrocarbon group, it may be long and have from 12 to 22 carbon atoms or be short and have from 1 to 3 carbon atoms.

When $R_{25}$ is an $R_{29}$ hydrocarbon-based group, it preferably contains 1 to 3 carbon atoms.

Advantageously, $R_{24}$, $R_{26}$ and $R_{28}$, which are identical or different, are chosen from saturated or unsaturated and linear or branched $C_{11}$-$C_{21}$ hydrocarbon groups and more particularly from saturated or unsaturated and linear or branched $C_{11}$-$C_{21}$ alkyl and alkenyl groups.

Preferably, x and z, which are identical or different, have values of 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a ($C_1$-$C_4$)alkyl sulfate or a ($C_1$-$C_4$)alkyl- or a ($C_1$-$C_4$)alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anionic counterion $X^-$ is even more particularly chloride, methyl sulfate or ethyl sulfate.

Use is made more particularly in the composition according to the invention of the ammonium salts of formula (A5) in which:
$R_{22}$ denotes a methyl or ethyl group,
x and y are equal to 1,
z is equal to 0 or 1,
r, s and t are equal to 2,
$R_{23}$ is chosen from:
the group

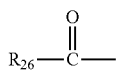

methyl, ethyl or $C_{14}$-$C_{22}$ hydrocarbon-based groups,
a hydrogen atom,
$R_{25}$ is chosen from:
the group

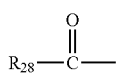

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based radicals are linear.

Among the compounds of formula (A5), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil, such as palm oil or sunflower oil. When the compound comprises several acyl groups, the latter can be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts comprising at least one ester functional group described in U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

The amphoteric or zwitterionic surfactant(s) used in step a) are preferably non-silicone surfactants. They may especially be aliphatic secondary or tertiary amine derivatives, in which the aliphatic group is a linear or branched chain containing 8 to 22 carbon atoms and containing at least one water-solubilizing anionic group, for instance a carboxylate, sulfonate, sulfate, phosphate or phosphonate group; mention may also be made of ($C_8$-$C_{20}$)alkylbetaines, sulfobetaines, ($C_8$-$C_{20}$)alkylamido($C_6$-$C_8$)alkylbetaines or ($C_8$-$C_{20}$)alkylamido($C_6$-$C_8$)alkylsulfobetaines; and mixtures thereof.

Among the optionally quaternized secondary or tertiary aliphatic amine derivatives that may be used, as defined above, mention may also be made of the compounds of respective structures (A6) and (A7) below:

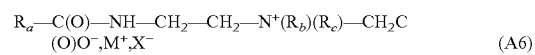

in which formula (A6):
Ra represents a C10-C30 alkyl or alkenyl group derived from an acid Ra—COOH preferably present in hydrolyzed copra oil, or a heptyl, nonyl or undecyl group;
Rb represents a β-hydroxyethyl group; and
Rc represents a carboxymethyl group;
M+ represents a cationic counterion derived from an alkali metal or alkaline-earth metal, such as sodium, an ammonium ion or an ion derived from an organic amine, and
$X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$) alkylaryl sulfonates, in particular methyl sulfate and ethyl sulfate; or alternatively $M^+$ and $X^-$ are absent;

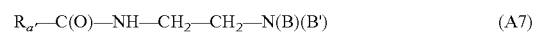

in which formula (A7):

B represents the group —CH$_2$—CH$_2$—O—X';

B' represents the group —(CH2)zY', with z=1 or 2;

X' represents the group —CH$_2$—C(O)OH, —CH$_2$—C(O)OZ', —CH$_2$—CH$_2$—C(O)OH or —CH$_2$—CH$_2$—C(O)OZ', or a hydrogen atom;

Y' represents the group —C(O)OH, —C(O)OZ', —CH$_2$—CH(OH)—SO$_3$H or the group —CH$_2$—CH(OH)—SO$_3$—Z';

Z' represents a cationic counterion derived from an alkali metal or alkaline-earth metal, such as sodium, an ammonium ion or an ion derived from an organic amine;

R$_{a'}$ represents a C$_{10}$-C$_{30}$ alkyl or alkenyl group derived from an acid R$_{a'}$—C(O)OH, which is preferably present in copra oil or in hydrolyzed linseed oil, an alkyl group, especially a C$_{17}$ group and its iso form, or an unsaturated C$_{17}$ group.

These compounds of formulae (A6) and (A7) are classified in the CTFA dictionary, 5th edition, 1993, under the names disodium cocoamphodiacetate, disodium lauroamphodiacetate, disodium caprylamphodiacetate, disodium caproamphodiacetate, disodium cocoamphodipropionate, disodium lauroamphodipropionate, disodium caprylamphodipropionate, disodium caproamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (A'2):

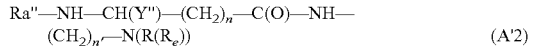

(A'2)

in which formula:

Y" represents the group —C(O)OH, —C(O)OZ", —CH$_2$—CH(OH)—SO$_3$H or the group —CH$_2$—CH(OH)—SO$_3$—Z";

Rd and Re represent, independently of each other, a C1-C4 alkyl or hydroxyalkyl radical;

Z" represents a cationic counterion derived from an alkali metal or alkaline-earth metal, such as sodium, an ammonium ion or an ion derived from an organic amine;

Ra" represents a C10-C30 alkyl or alkenyl group derived from an acid

Ra"—C(O)OH, which is preferably present in hydrolyzed linseed oil or copra oil.

n and n' denote, independently of each other, an integer ranging from 1 to 3.

Among the compounds of formula (A'2), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of (C$_8$-C$_{20}$)alkylbetaines such as cocobetaine, (C$_8$-C$_{20}$)alkylamido(C$_3$-C$_8$)alkylbetaines such as cocamidopropylbetaine, compounds of formula (B'2) such as the sodium salt of diethylaminopropyl lauraminosuccinamate (INCI name: sodium diethylaminopropyl cocoaspartamide), and mixtures thereof.

Preferably, the surfactant(s) may be chosen from nonionic surfactants, amphoteric or zwitterionic surfactants and cationic surfactants, which may be silicone or non-silicone surfactants.

Steps b) and c)

The cosmetic process for treating keratin fibers according to the invention especially comprises steps b) and c) consisting, respectively, in applying a mechanical tension to these keratin fibers and in exposing them under mechanical tension to microwaves at a pressure ranging from 50 000 to 250 000 Pa and better still from 75 000 to 150 000 Pa, better still at atmospheric pressure in the presence of at least one solvent in vapor form on contact with said keratin fibers and without there being complete drying of the keratin fibers throughout the entire exposure to the microwaves.

In the event of complete drying in step c), no shaping is obtained.

Consequently, especially when steps a), b) and c) are performed in this order, a step consisting in applying again a certain amount of the composition from step a) or a certain amount of solvent may be performed just before step c) (in order to ensure that the keratin fibers are kept moist).

It is understood that when such a step of applying a composition from step a) is again performed before step c), said composition contains the same substance as that which had been applied during step a), i.e.:

it contains at least one fatty substance when the composition from step a) contains at least one fatty substance, it contains at least one non-silicone polymer when the composition from step a) contains at least one non-silicone polymer, and it contains at least one surfactant when the composition from step a) contains at least one surfactant.

During step b), the microwave radiation may or may not already exist, and this is likewise the case for the solvent in vapor form. In other words, step b) is prior to or simultaneous with step c).

The expression "mechanical tension applied to the hair" should be understood as meaning a mechanical tension applied to at least a portion of the length of said hair.

The term "microwaves" should be understood as meaning electromagnetic radiation with a frequency of between 500 MHz and 300 GHz.

The microwave frequency used in step c) is preferentially between 500 MHz and 300 GHz, for example ranging from 500 MHz to 10 GHz and in particular from 915 MHz to 2.45 GHz.

The microwave power used in step c) may range from 100 to 2000 W, preferably from 100 to 500 W and more particularly from 180 to 450 W.

The microwaves may be generated by a microwave generator, for example a solid-state generator such as a magnetron.

The expression "without there being complete drying of the hair" means that after step c) the hair feels wet. The hair may thus conserve at least 1%, especially at least 2% or even 5% of the weight of the liquid compounds (solvents) present, before step c), on contact therewith, these liquid compounds adding to the natural humidity of the hair before treatment.

The mechanical tension may be applied by means of a device for applying a mechanical tension, this device possibly being configured to induce flexure, traction, torsion and/or compression, for example, on the hair. The device for applying a mechanical tension may exert mechanical constraints simultaneously on one or more locks of hair.

The mechanical tension device may be, for example, a curler.

The solvent in vapor form is entirely generated by evaporating a compound present, before emission of the microwaves, on contact with the treated hair.

The treated hair should never be totally dry throughout the entire action of the microwaves. In other words, the hair should always be impregnated with the solvent during said exposure.

To facilitate the impregnation, the solvent may be sprayed on beforehand.

Step c) of the process according to the invention may take place in a chamber optionally along with step b); in addition, steps b) and c) may be performed in one and the same chamber. The chamber may form a microwave shield.

The chamber may, during the process according to the invention, especially during step c), contain the hair to be treated and the device for applying a mechanical tension.

The term "contain the hair" should be understood as meaning contain the hair over all or part of its length.

The chamber may cover the hair over a length, for example, of greater than or equal to 5 cm. Thus, a length of at least 5 cm of hair may be treated in the chamber.

The chamber may be immobile relative to the hair treated during the emission of the microwaves or mobile relative to the hair, for example being moved along the hair to be treated.

The microwaves may be emitted, where appropriate, from an antenna.

As indicated previously, the chamber may be configured so as not to release into the external medium the solvent in vapor form, or so as to release only a small amount thereof, for example by means of recycling of the solvent, the recycling taking place, for example, in vapor or liquid form, after condensation of the solvent.

The chamber may comprise a material configured to absorb the solvent in vapor form. The chamber may comprise a cold wall on which the solvent condenses and/or a loop for sucking up solvent in vapor form.

Thus, the process according to the invention may comprise, during and/or after step c), a step of collecting solvent, for example in vapor and/or liquid form and/or absorbed on a material.

The chamber is advantageously substantially microwave-leaktight. In other words, the chamber may be configured to contain the microwaves emitted. Step c) may thus take place in a chamber that is microwave-leaktight.

The chamber may comprise at least one seal of an electrically conductive material, which is, for example, elastically deformable, making it possible to block the microwaves used during step c) while allowing the hair to leave the chamber, if necessary. The seal may comprise, for example, a foam filled with electrically conductive particles, a brush formed from electrically conductive bristles or a comb comprising metal teeth.

When the chamber is in the form of a hood, the chamber may comprise electromagnetic shielding through which the treated hair may pass. Such shielding makes it possible to treat the user's hair while protecting the user's skull from the microwaves emitted.

The electromagnetic shielding may be formed, for example, by a grate or a metallic grating.

The treatment device for performing the process may comprise an audible and/or visible warning system, for example for warning the user of a microwave leak out of the chamber and/or of an excessive temperature inside the chamber. The treating device advantageously comprises a safety system for preventing the emission of microwaves while the chamber is not closed and/or in the event of abnormal functioning, for example of excessive temperature and/or in the absence of solvent.

The treating device may be configured to control the duration of emission of the microwaves, so as not to reach a duration of treatment that is liable to damage the hair.

The process according to the invention may comprise, before step c), a step of detecting the closure of the chamber. For example, a contactor is actuated when the chamber is closed.

The emission of the microwaves may be conditioned to the detection of closure of the chamber.

The process according to the invention may also comprise a step of detecting the emplacement of the hair intended to be treated, before step c). This detection step may be performed, for example, by an optical sensor and/or a mechanical feeler.

The process according to the invention may comprise, for example during step c), a step of measuring the temperature to which the treated hair is subjected. This temperature measurement step may be performed by a thermometer without contact with the hair.

The chamber, for example when it is defined by tongs, may include all or part of the device for applying the mechanical tension.

The device for applying the mechanical tension may comprise one or more curlers or other rolling device, which are, for example, electrically insulating and compatible with exposure to microwaves, jaws and/or one or more combs.

The treating device may be configured to allow the use of several different constraint-application devices, serving, for example, to curl the hair or, on the contrary, to straighten it. The devices may be interchangeable by the user.

The treating device may be arranged to automatically recognize the constraint-application device used, where appropriate, for example by means of electrical contacts or one or more switches.

The device for applying the mechanical tension may be configured so as to place the treated hair flat during the exposure to the microwaves.

Irrespective of the embodiment under consideration, the hair treated in step b) may be subjected to one or more mechanical constraints. The mechanical constraint(s) may be chosen from bending, straightening, compression, torsion and/or traction constraints.

The constraints applied may be intended to curl the hair or, on the contrary, to straighten it. The constraints applied may also be intended to curl the hair over one portion of its length and to straighten it over another portion of its length.

According to a particular embodiment of the invention, step b) is performed by applying at least one torsion, traction or compression constraint on the keratin materials.

The treating device may comprise, within the same hand-held piece, the microwave generator and the device for applying the mechanical tension. The term "hand-held piece" denotes a piece manipulated by the user in one hand during the hair treatment.

When the treating device comprises tongs, the microwaves may be emitted by only one of the arms of the tongs or by all the arms of the tongs.

As conveying means that may be used for conveying the microwaves from the generator to the chamber, mention may be made of waveguides, for example a flexible coaxial cable less than 10 m long, preferably less than 5 m long, less than 5 cm and preferably less than 2 cm in diameter, and assemblies comprising at least one antenna for emitting electromagnetic radiation and at least one antenna for receiving electromagnetic radiation.

The microwave generator and/or the chamber may be configured to subject the hair treated in step c) to microwave radiation that is variable in its spatial distribution within the chamber, for example rotating. Rotating microwave radiation may advantageously make it possible to expose the treated hair more uniformly to said radiation and thus to reduce the risk of local overexposure to the radiation.

The solvent(s) are, for example, liquids with a boiling point of less than 200° C.

Said solvent may be, for example, and preferably is contained in the composition comprising at least one fatty substance from step a).

Said solvent may comprise and in particular may consist of a polar protic liquid medium with a dielectric constant at 20° C. of greater than or equal to 8, preferably greater than or equal to 10 and in particular greater than or equal to 15.

According to a preferred embodiment, the solvents used comprise water. Even more preferentially, the solvent used is water.

According to another preferred embodiment, this solvent is propanol or isopropanol.

According to yet another preferred embodiment, the solvents consist of a mixture of water and of propanol or isopropanol.

In one embodiment, the solvent in vapor form may be generated by direct heating of the solvent in liquid form by the microwaves.

The solvents in vapor form may have, in the region of and/or in contact with the hair, during step c), a temperature of between 80 and 200° C. and preferably between 100 and 150° C., for example between 120 and 150° C.

The pressure to which the treated hair is subjected, during step c) is close to atmospheric pressure, and may range from 50 000 to 250 000 Pa and better still from 75 000 to 150 000 Pa.

The hair may, during part or all of step c), be present in a volume defined by at least one wall of a material, said material allowing the microwaves to pass through the wall and limiting the evaporation of the compound present, before emission of the microwaves, on contact with the treated hair.

The use of such a material may advantageously limit the drying of the hair during the treatment according to the invention.

Said material may comprise and in particular may consist of cellophane and/or may have a low porosity. In one variant, the material may be porous and in particular may be a mesh.

Irrespective of the embodiment under consideration, the duration of step c) may range from 1 second to 60 minutes, preferably from 1 second to 30 minutes, better still from 30 seconds to 20 minutes and more particularly from 3 to 15 minutes.

Irrespective of the embodiment under consideration, step c) may be repeated, for example between 0 and 10 times and preferentially between 0 and 5 times.

DESCRIPTION OF THE FIGURES

The invention may be better understood from reading the following detailed description of nonlimiting implementation examples thereof, and with reference to the attached drawing, in which:

FIGS. 1 to 5 schematically and partially show embodiments of treating devices according to the invention.

FIG. 1 shows a treating device 100 comprising a hand-held piece 3 comprising a chamber in which is received the hair to be treated, connected via a hose 2 to a base station 1 comprising a microwave generator.

Figure 6:
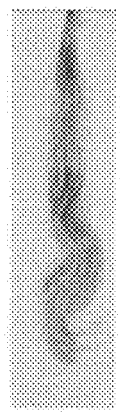
FIGS. 6, 7 and 9 to 13 show locks of hair that have undergone various cosmetic treatments according to the process of the invention, FIG. 8 schematically and partially shows an embodiment according to the invention.

The hose 2 may comprise a waveguide.

FIG. 2 shows a detail of FIG. 1.

The microwaves 70 conveyed into the hand-held piece 3 by the waveguide 2 make it possible to heat the liquid solvent present on the hair to be treated and to change it into the form of solvent in vapor form. In this embodiment, a device for applying a mechanical tension and a lock of hair (not shown) are present in the hand-held piece 3 and the hair is exposed both to the microwaves and to the solvent in vapor form 80. A temperature detector 150 may be present in order to measure the temperature of the treated lock of hair and a control system, for example a microprocessor system, may make it possible to interrupt or modify the emission of the microwaves in the event of a detected temperature being above a predefined threshold.

FIG. 3 shows an embodiment in which the treating chamber is formed by closing tongs constituting all or part of the hand-held piece 3. The tongs make it possible, when open, to introduce between the arms one or more locks of hair to be treated. Each arm defines, for example, half of the chamber.

The microwaves may be emitted by only one or by both arms of the tongs.

A sensor (not shown) may inform the treating device regarding the fact that the tongs are closed and the emission of the microwaves may be conditioned to the detection of this closure.

The mechanical tension applied to the hair may be a traction so as to straighten it.

In all the preceding examples, the means for conveying the microwaves may comprise an emitting antenna 10 and a receiving antenna 15, as illustrated in FIG. 4.

FIG. 5 moreover shows a lock of hair M present in a treating chamber of the hand-held piece 3. The chamber is microwave-leaktight and comprises, to this end, for example, electrically conductive foam seals 200 which reflect the microwave radiation where the hair leaves the chamber.

In one variant, not shown, the microwave generator 1 may, for example, be present in the chamber and/or the device for applying a mechanical tension.

FIG. 8 shows an embodiment in which a lock of hair M is present in a volume delimited by a wall 300 of a material, said material allowing the microwaves 70 to pass through the wall, and containing the generated vapor 80.

The contents of the vapor 80 advantageously allow the hair M to be moistened during the treatment.

Said material comprises and in particular consists of a cellophane film. In one variant, the material may be porous and in particular may be a mesh.

Steps d) and e)

The process according to the invention may also comprise at least one additional pretreatment step d) and/or one additional post-treatment step e), these steps consisting in performing on the keratin materials at least one standard treatment chosen from oxidation dyeing, direct dyeing, bleaching, permanent reshaping based on one or more reducing agents, for example thiol reducing agents, or based on one or more alkali metal or alkaline-earth metal hydroxides, a care treatment, a mask and/or a shampoo.

Advantageously, when the composition from step a) is a composition containing at least one fatty substance, the composition(s) applied during the additional step(s) d) are free of fatty substances.

Advantageously, when the composition from step a) is a composition containing at least one fatty substance, the composition(s) applied during the additional step(s) e) are free of fatty substances.

Advantageously, when the composition from step a) is a composition containing at least one non-silicone polymer, the composition(s) applied during the additional step(s) d) are free of non-silicone polymer.

Advantageously, when the composition from step a) is a composition containing at least one non-silicone polymer, the composition(s) applied during the additional step(s) e) are free of non-silicone polymer.

Advantageously, when the composition from step a) is a composition containing at least one surfactant, the composition(s) applied during the additional step(s) d) are free of surfactant.

Advantageously, when the composition from step a) is a composition containing at least one surfactant, the composition(s) applied during the additional step(s) e) are free of surfactant.

Step d) takes place before steps a), b) and c).

Step e) takes place after steps a), b) and c).

When an additional pretreatment step d) and an additional post-treatment step e) are performed, these steps may be identical or different, and are preferably different.

According to a preferred embodiment of the invention, the additional step is a pretreatment step d).

When the additional step is a step comprising permanent reshaping based on one or more reducing agents, then the step may be followed by a step comprising the application to the hair of at least one fixing composition comprising one or more oxidizing agents.

Advantageously, the composition(s) applied during the additional step(s) d) are free of alkali metal or alkaline-earth metal hydroxides at a pH above 12 or of reducing agents for cleaving the disulfide bonds.

Advantageously, the composition(s) applied during the additional step(s) e) are free of alkali metal or alkaline-earth metal hydroxides at a pH above 12 or of reducing agents for cleaving the disulfide bonds.

The duration of step d) may vary according to the desired shaping performance qualities and the nature of the hair, for example.

The composition used in step a) and the optional compositions used in the additional steps d) and e) may be applied while the hair is present in the chamber, for example by means of a suitable application system. The application system comprises, for example, a pad, a comb, one or more dispensing orifices or a spray nozzle, arranged in the chamber or outside it, for example on the path of the hair leaving or entering the chamber.

The composition used in step d) may be subjected to the microwave radiation.

The treatment device may comprise a sensor that is sensitive to a characteristic of the hair, for example the color, the mechanical strength, the surface state or the humidity, and the treating device may control at least one parameter of the treatment as a function of the characteristic thus detected, for example the microwave energy, the solvent temperature, the duration of the treatment and/or the mechanical constraint exerted.

According to another of its aspects, the present invention relates to a hair treatment device for performing the process as defined above, comprising:
- a device for applying a mechanical tension to the hair,
- a microwave generator,
- at least one composition comprising at least one substance chosen from fatty substances, silicone polymers and surfactants.

All the characteristics stated with regard to the above process apply to the treating device.

Thus, the treating device may, for example, define a treating chamber forming a shield to microwaves.

All the compositions used in the process according to the invention may be, independently of each other, in the form of a thickened or unthickened lotion, a cream, a gel or a mousse.

The examples that follow are given as nonlimiting illustrations of the present invention.

EXAMPLES

Example 1

Process for Durably Curling the Hair Using a Composition Containing at Least One Fatty Substance A 1 g lock 20 cm long of moistened natural straight hair was treated in the following manner.

The lock is shampooed and dried manually, and an aqueous composition in accordance with the invention comprising at least one fatty substance is then applied, with a minimum bath ratio of 2 to 1, uniformly along the lock.

The lock is then rolled up on and fixed to a curler.

The lock is then placed in a confined medium (such as cellophane) or not, and is then treated by the emission of microwaves via a household microwave device (Samsung Combi CE 137 nem; 2.45 GHz) for 15 minutes with a power of 300 W.

The end of the treatment is followed by rinsing or shampooing, depending on the case.

The table that follows indicates the aqueous composition applied.

| Constituents - | Amount in weight percentage (commercial product as is) |
|---|---|
| Cetearyl alcohol (Ecorol 68/50 P from Ecogreen Oleochemicals) | 5 |
| Cetyl esters (Crodamol MS-PA-(MH) from Croda) | 1 |
| Behentrimonium chloride (Varisoft BT 85 (flaked) from Evonik Goldschmidt) | 1 |
| Amodimethicone (and) Trideceth-6 (and) cetrimonium chloride (Xiameter MEM-8299 Emulsion from Dow Corning) | 1.5 |
| Water | qs 100 |

This process allows shaping of the lock (which is initially straight), the lock obtained is durably curled, and a gain in the volume of the lock is also observed.

The result is reported in FIG. 6.

Example 2

Process for Durably Curling the Hair Using a Composition Containing at Least One Fatty Substance A 1 g lock 20 cm long of moistened natural straight hair was treated in a manner similar to that of Example 1, except that the aqueous composition applied here is that detailed in the following table.

| Constituents-INCI name | Amount in weight percentage (commercial product as is) |
| --- | --- |
| Beeswax (White beeswax GR B 889 from Koster Keunen) | 1.5 |
| Mineral oil (and) microcrystalline wax (and) paraffin (Vaseline Blanche Codex 236 from Aiglon) | 6.5 |
| Mineral oil (Blandol from Sonneborn) | 16 |
| Cetearyl alcohol (Ecorol 68/50 P from Ecogreen Oleochemicals) | 2 |
| Propylene glycol USP/EP from Dow Chemical | 5 |
| Water | qs 100 |

This process allows shaping of the lock, the lock obtained is durably curled, and a gain in the volume of the lock is also observed.

Figure 7:
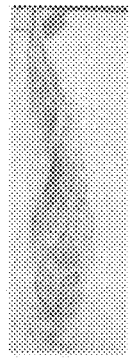

The result is reported in FIG. 7.

Example 3

Process for Durably Curling the Hair Using a Composition Containing at Least One Non-Silicone Polymer A 1 g lock 20 cm long of moistened natural straight hair was treated in the following manner.

The lock is shampooed and dried manually, and an aqueous composition in accordance with the invention comprising at least one non-silicone polymer is then applied, with a minimum bath ratio of 2 to 1, uniformly along the lock.

The lock is then rolled up on and fixed to a curler.

The lock is then placed in a confined medium (such as cellophane), and is then treated by the emission of microwaves via a household microwave device (Samsung Combi CE 137 nem; 2.45 GHz) for 5 minutes with a power of 450 W.

The end of the treatment is followed by rinsing or shampooing, depending on the case.

The table that follows indicates the aqueous composition applied.

| Constituents | Amount in weight percentage (commercial product as is) |
| --- | --- |
| Potato starch modified (Structure Solanace from Akzo Nobel) | 0.3 |
| Carbomer (Carbopol Ultrez 10 Polymer from Lubrizol) | 0.45 |
| Hydroxypropyl guar (Jaguar HP 105 from Rhodia) | 0.25 |
| Polyquaternium-4 (Celquat LOR from Akzo Nobel) | 0.3 |
| Behentrimonium chloride (Varisoft BT 85 (flaked) from Evonik Goldschmidt) | 0.5 |
| Cetyl alcohol (and) behentrimonium methosulfate (and) Quaternium-33 (Cutissential Behenyl 18MEA-PA-(MH) from Croda) | 0.1 |
| Propylene glycol (Propylene glycol USP/EP from Dow Chemical) | 2.5 |
| 2-Oleamido-1,3-octadecanediol (Mexanyl GZ from Chimex) | 0.01 |
| Quaternium-87 (Varisoft W 575 PG N from Evonik Goldschmidt) | 0.05 |
| Cyclopentasiloxane (and) dimethiconol (Xiameter PMX-1501 Fluid from Dow Corning) | 6 |
| PEG/PPG-17/18 Dimethicone | 0.5 |
| Amodimethicone (and) Trideceth-6 (and) cetrimonium chloride | 0.25 |
| Triethanolamine | 0.6 |
| Water | qs 100 |

Figure 9:
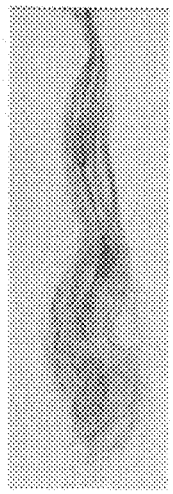

This process allows shaping of the lock (which is initially straight), the lock obtained is durably curled, and a gain in the volume of the lock is also observed. The result is reported in FIG. 9.

Example 4

Process for Durably Curling the Hair Using a Composition Containing at Least One Non-Silicone Polymer A 1 g lock 20 cm long of moistened natural straight hair was treated in a manner similar to that of Example 1, using the aqueous composition detailed in the following table.

| Constituents | Amount in weight percentage (commercial product as is) |
| --- | --- |
| Methylisothiazolinone (Neolone 950 Preservative from Rohm & Haas (Dow Chemical)) | 0.1 |
| Caprylyl glycol (Dermosoft Octiol from Dr. Straetmans) | 0.4 |
| Acrylates/C10-30 alkyl acrylate crosspolymer (Pemulen TR-1 Polymer from Lubrizol) | 1.4 |
| VP/VA copolymer (Luviskol VA 64 W from BASF) | 10 |
| VP/dimethylaminoethyl methacrylate copolymer (Copolymer 845-O from ISP (Ashland)) | 12 |
| PEG-40 hydrogenated castor oil (Eumulgin HRE 40 from Cognis (BASF)) | 1 |
| Niacinamide (Niacinamide USP from Lonza) | 0.1 |
| Panthenol (Dexpanthenol from Daiichi Fine Chemical) | 0.1 |
| Water | qs 100 |

This process allows shaping of the lock, the lock obtained is durably curled, and a gain in the volume of the lock is also observed.

Figure 10:
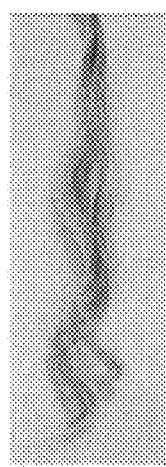

The result is reported in FIG. 10.

Example 5

Process for Durably Curling the Hair Composition Containing at Least One Non-Silicone Polymer A 1 g lock 20 cm long of moistened natural straight hair was treated in a manner similar to that of Example 1, using the aqueous composition detailed in the following table.

| Constituents | Amount in weight percentage (commercial product as is) |
|---|---|
| Ethanolamine (Monoethanolamine Care from BASF) | 0.47 |
| Oleth-30 (Eumulgin O 30 from Cognis (BASF)) | 4.5 |
| Laureth-12 (Rewopal 12 from Evonik Goldschmidt) | 6.3 |
| Deceth-5 (Eumulgin BL 589 from Cognis (BASF)) | 4.5 |
| Deceth-3 (Eumulgin BL 309 from Cognis (BASF)) | 17.2 |
| Oleyl alcohol (HD Ocenol 80/85V from Cognis (BASF)) | 1.8 |
| Trideceth-2 carboxamide MEA (Amidet A15/LAO 55 from KAO) | 4 |
| Hexadimethrine chloride (Mexomere PO from Chimex) | 3 |
| Polyquaternium-22 (Merquat 280 Polymer from Nalco (Lubrizol)) | 3 |
| Glycerol (Glycerin 99.8% PF from Emery Oleochemicals) | 3 |
| Ammonium thiolactate (Ammonium thiolactate 58% (50% ATL) from Bruno Bock) | 0.8 |
| Water | qs 100 |

This process allows shaping of the lock, the lock obtained is durably curled, and a gain in the volume of the lock is also observed.

Figure 11:
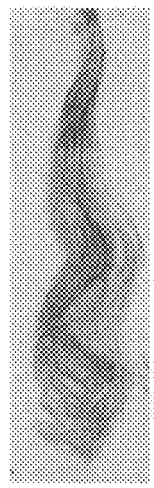

The result is reported in FIG. 11.

Example 6

Process for Durably Curling the Hair Using a Composition Containing at Least One Surfactant A 1 g lock 20 cm long of moistened natural straight hair was treated in the following manner.

The lock is shampooed and dried manually, and an aqueous composition in accordance with the invention comprising at least one surfactant is then applied, with a minimum bath ratio of 2 to 1, uniformly along the lock.

The lock is then rolled up on and fixed to a curler.

The lock is then placed in a confined medium (such as cellophane film), and is then treated by the emission of microwaves via a household microwave device (Samsung Combi CE 137 nem; 2.5 GHz) for 5 minutes with a power of 450 W.

The end of the treatment is followed by rinsing or shampooing, depending on the case.

The table that follows indicates the aqueous composition applied.

| Constituents | Amount in weight percentage (commercial product as is) |
|---|---|
| Deceth-3 (Eumulgin BL 309 from Cognis (BASF)) | 22 |
| Deceth-5 (Eumulgin BL 589 from Cognis (BASF)) | 19.5 |
| Cocamide MIPA (and) isopropanolamine (Rewomid V 3203 from Evonik Goldschmidt) | 7.2 |
| Propylene glycol USP/EP (from Dow Chemical) | 15 |
| Hexylene glycol from Rhodia | 1 |
| Hydroxyethyl oleyl dimonium chloride as a 30% aqueous solution | 3.33 |
| Sodium metabisulfite from BASF | 0.455 |
| Erythorbic acid from Zhengzou Tuoyang Bioengineering | 0.31 |
| Water | qs 100 |

This process allows shaping of the lock (which is initially straight), the lock obtained is durably curled, and a gain in the volume of the lock is also observed.

Figure 12:
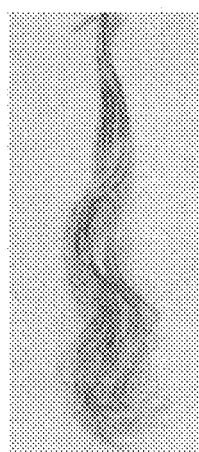

The result is reported in FIG. 12.

Example 7

Process for Durably Curling the Hair Using a Composition Containing at Least One Surfactant A 1 g lock 20 cm long of moistened natural straight hair was treated in a manner similar to that of Example 1, except that the aqueous composition applied here is that detailed in the following table.

| Constituents | Amount in weight percentage (commercial product as is) |
|---|---|
| Potato starch modified (Structure Solanace from Akzo Nobel) | 0.3 |
| Carbomer (Carbopol Ultrez 10 Polymer from Lubrizol) | 0.38 |
| Hydroxypropyl guar (Jaguar HP 105 from Rhodia) | 0.25 |
| Polyquaternium-4 (Ceresin Wax SP 254P from Strahl & Pitsch) | 0.3 |
| Behentrimonium chloride (Varisoft BT 85 (flaked) from Evonik Goldschmidt) | 0.5 |
| Propylene glycol USP/EP (from Dow Chemical) | 2.5 |
| Cyclopentasiloxane (and) dimethiconol (Xiameter PMX-1501 Fluid from Dow Corning) | 10.6 |
| PEG/PPG-17/18 Dimethicone (Xiameter OFX-5220 Fluid from Dow Corning) | 0.5 |
| Water | qs 100 |

This process allows shaping of the lock, the lock obtained is durably curled, and a gain in the volume of the lock is also observed.

Figure 13:
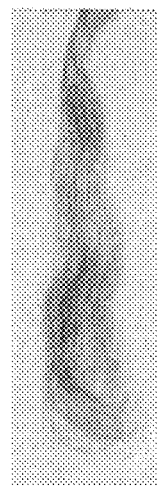

The result is reported in FIG. 13.

The invention claimed is:

1. A cosmetic process for treating keratin fibers, comprising:
    a) applying to said keratin fibers a composition comprising at least one of a fatty substance said composition being free of alkali metal or alkaline-earth metal hydroxide at a pH above 12 or being free of reducing agents for cleaving disulfide bonds,
    b) applying a mechanical tension to said keratin fibers, and c) exposing said keratin fibers under mechanical tension to microwaves, at a pressure ranging from 50 000 to 250 000 Pa, in the presence of at least one solvent that compromises water in vapor form on contact with the keratin fibers and without there being complete drying of the keratin fibers throughout the entire exposure to the microwaves, wherein the at least one solvent in vapor form being entirely generated by evaporating at least one solvent present, before emission of the microwaves, on contact with the keratin fibers, and a) place prior to c).

2. The process as claimed in claim 1, in which the pressure ranges from 75 000 to 150 000 Pa.

3. The process as claimed in claim 1, in which said fatty substance(s) are chosen from $C_6$-$C_{16}$ hydrocarbons, hydrocarbons containing more than 16 carbon atoms, non-silicone oils of animal origin, triglyceride plant oils, synthetic triglycerides, fluoro oils, fatty alcohols, non-salified fatty acids, fatty acid, fatty alcohol esters other than triglycerides, plant waxes, non-silicone waxes, silicones, and mixtures thereof.

4. The process as claimed in claim 1, in which the fatty substance(s) are chosen from hydrocarbon waxes, plant waxes, solid fatty alcohols, solid esters of fatty acids, of fatty alcohols, and mixtures thereof.

5. The process as claimed in claim 1, in which the composition in a) is an aqueous composition.

6. The process as claimed in claim 1, in which a) is prior to b).

7. The process as claimed in claim 1, in which b) is performed by applying at least one torsion, traction or compression constraint on the keratin materials.

8. The process as claimed in claim 1, in which the duration of c) ranges from 1 second to 60 minutes.

9. The process as claimed in claim 1, further comprising, before a), after c), or both before a) and after c), at least one treatment chosen from oxidation dyeing, direct dyeing, bleaching, permanent reshaping comprising one or more reducing agents, permanent reshaping comprising on one or more alkali metal, permanent reshaping comprising alkaline-earth metal hydroxides, a mask and a shampoo.

10. The process as claimed in claim 1, wherein said keratin fibers are hair.

* * * * *

UNITED STATES PATENT AND TRADEMARK OFFICE
CERTIFICATE OF CORRECTION

PATENT NO. : 9,572,412 B2
APPLICATION NO. : 14/406056
DATED : February 21, 2017
INVENTOR(S) : Gabin Vic et al.

Page 1 of 1

It is certified that error appears in the above-identified patent and that said Letters Patent is hereby corrected as shown below:

In the Claims

Column 47, Line 12, "a) place prior to c)." should read --a) is prior to c).--

Signed and Sealed this
First Day of May, 2018

Andrei Iancu
*Director of the United States Patent and Trademark Office*